US012576122B2

(12) United States Patent
Amin

(10) Patent No.: US 12,576,122 B2
(45) Date of Patent: *Mar. 17, 2026

(54) COMBINATION THERAPY FOR CANCER

(71) Applicant: United Arab Emirates University, Al Ain (AE)

(72) Inventor: Amr Amin, Al Ain (AE)

(73) Assignee: UNITED ARAB EMIRATES UNIVERSITY, Al Ain (AE)

( * ) Notice: Subject to any disclaimer, the term of this patent is extended or adjusted under 35 U.S.C. 154(b) by 0 days.

This patent is subject to a terminal disclaimer.

(21) Appl. No.: 16/272,515

(22) Filed: Feb. 11, 2019

(65) Prior Publication Data

US 2020/0254049 A1     Aug. 13, 2020

Related U.S. Application Data

(63) Continuation of application No. 16/272,426, filed on Feb. 11, 2019, now Pat. No. 12,521,425.

(51) Int. Cl.
| | |
|---|---|
| *A61K 36/88* | (2006.01) |
| *A61K 31/11* | (2006.01) |
| *A61K 31/4745* | (2006.01) |
| *A61K 45/06* | (2006.01) |
| *A61P 35/00* | (2006.01) |

(52) U.S. Cl.
CPC .............. *A61K 36/88* (2013.01); *A61K 31/11* (2013.01); *A61K 31/4745* (2013.01); *A61K 45/06* (2013.01); *A61P 35/00* (2018.01)

(58) Field of Classification Search
CPC .... A61K 31/4745; A61K 31/11; A61K 31/44; A61K 36/88; A61P 35/00
See application file for complete search history.

(56) References Cited

PUBLICATIONS

Alexandre et al., Combination of Topotecan and Oxaliplatin in Inoperable Hepatocellular Cancer Patients. Am. J. Clin. Oncol., 25(2), 198-203 (Year: 2002).*
Mlynarczyk & Fahraeus, "Endoplasmic reticulum stress sensitizes cells to DNA damage-induced apoptosis through b53-dependent suppression of p21 CDKN1A", Nature Communications, 2014, 16 pages.
Mihailidou et al., "CHOP-dependent regulation of p21/waf1 during ER stress", Cellular Physiology and Biochemistry, 2010, vol. 25, pp. 761-766, 6 pages.
Maytin et al., "Stress-inducible transcription factor CHOP/gadd153 induces apoptosis in mammalian cells via p38 kinase-dependent and -independent mechanisms", Experimental Cell Research, 2001, vol. 267, pp. 193-204, 12 pages.
Hamanaka et al., "PERK and GCN2 contribute to eIF2alpha phosphorylation and cell cycle arrest after activation of the unfolded protein response pathway", Molecular Biology of the Cell, 2005, vol. 16, pp. 5493-5501, 9 pages.

Ng et al., "Curcumin sensitizes acute promyelocytic leukemia cells to unfolded protein response-induced apoptosis by blocking the loss of misfolded N-CoR protein" Molecular Cancer Research, 2011, vol. 9, pp. 878-888, 12 pages.
Huang et al., "Anacardic acid induces cell apoptosis associated with induction of ATF4-dependent endoplasmic reticulum stress", ELSEVIER, Toxicology Letters, 2014, vol. 228, pp. 170-178, 9 pages.
Teske et al., "The eIF2 kinase PERK and the integrated stress response facilitate activation of ATF6 during endoplasmic reticulum stress", MBoC|Article, Molecular Biology of the Cell, 2011, 22, 4390-4405, 16 pages.
Estornes et al., "RIPK1 promotes death receptor-independent caspase-8-mediated apoptosis under unresolved ER stress conditions", Cell Death and Disease, 2014, vol. 5, e1555, 11 pages.
Jimbo et al., "ER stress induces caspase-8 activation, stimulating cytochrome c release and caspase-9 activation", Experimental Cell Research, Science Direct, 2003, vol. 283, pp. 156-166, 11 pages.
Turlaro & Muñoz-Pinedo, "C. Cell death induced by endoplasmic reticulum stress", FEBS Journal 283, 2015, pp. 2640-2640, 13 pages.
Hiss & Gabriels, "Implications of endoplasmic reticulum stress, the unfolded protein response and apoptosis for molecular cancer therapy. Part I: targetingp53, Mdm2, GADD153/CHOP, GRP78/ BIP and heat shock proteins", Expert Opinion Drug Discovery, 2009, vol. 4, pp. 799-821, 23 pages.
Nalepa et al., "Drug discovery in the ubiquitin-proteasome system", . Nature Reviews Drug Discovery, 2006, vol. 6, pp. 596-613, 19 pages.
Zavrski et al., "Molecular and clinical aspects of proteasome inhibition in the treatment of cancer", Recent Results Cancer Research, 2007, vol. 176, pp. 165-176, 13 pages.
Saleh et al., "Antagonism between curcumin and the topoisomerase II inhibitor etoposide: A study of DNA damage, cell cycle regulation and death pathways", Cancer Biology & Therapy, 2012, vol. 13, pp. 1058-1071, 14 pages.
Krämer et al., "Causal analysis approaches in Ingenuity Pathway Analysis", Bioinformatics, vol. 30, No. 4, pp. 523-530, 8 pages.
Ahmad et al., "Role of traditional Islamic and Arabic plants in cancer therapy", Journal of Traditional and Complementary Medicine, 2017, vol. 7, pp. 195-204, 10 pages.
Aldridge et al., "The use of total protein stains as loading controls: an alternative to high-abundance single protein controls in semi-quantitative immunoblotting", Journal of Neuroscience Methods, 2008, vol. 172, No. 2, pp. 250-254, 10 pages.
Al-Hrout et al., "Safranal induces DNA double-strand breakage and ERstress-mediated cell death in hepatocellular carcinoma cells", Scientific Reports, 2018, vol. 8, 15 pages.

(Continued)

*Primary Examiner* — Clinton A Brooks
*Assistant Examiner* — Kyle Nottingham
(74) *Attorney, Agent, or Firm* — MH2 Technology Law Group, LLP

(57) ABSTRACT

Methods of treating, suppressing, or reducing the severity of a liver cancer in a subject are described herein. The disclosed methods include administering to the subject a first amount of safranal or a pharmaceutically acceptable pro-drug thereof and administering to the subject a second amount of a TOP1 inhibitor. In some embodiments, the TOP1 inhibitor is irinotecan, topotecan, camptothecin, lamellarin D, and/or combinations thereof.

3 Claims, 29 Drawing Sheets

(56)                    References Cited

PUBLICATIONS

Alsaied et al., "Sorafenib and triptolide as combination therapy for hepatocellular carcinoma", Surgery, 2014, vol. 156, No. 2, pp. 270-279, 10 pages.

Amin et al., "Saffron: a potential candidate for a novel anticancer drug against hepatocellular carcinoma", Hepatology Malignancies, 2011, vol. 54, No. 3, pp. 857-867, 11 pages.

Apel et al., "Phenanthrene derivatives from Appendicula reflexa as new CDK1/cyclin B inhibitors", ELSEVIER, Phytochemistry Letters, 2012, vol. 5, No. 4, pp. 814-818, 5 pages.

Bi, et al., "Identification of Caspase-6 and Caspase-7 from miiuy croaker and evolution analysis in fish", ELSEVIER, Fish & Shellfish Immunology, Science Direct, 2018, vol. 83, pp. 406-409, 4 p.

Chaitanya et al., "PARP-1 cleavage fragments: signatures of cell-death proteases in neurodegeneration", Cell Communication and Signaling, 2014, vol. 8, No. 31, 11 pages.

Crissien & Frenette, "Current Management of Hepatocellular Carcinoma", Gastroenterology & Hepatology, 2014, vol. 10, No. 3, pp. 153-161, 9 pages.

Fanale et al., "Stabilizing versus destabilizing the microtubules: a double-edge sword for an effective cancer treatment option?", Review Article, Analytical Cellular Pathology, 2015, vol. 2015, 19 pages.

Ferlay et al., "Cancer incidence and mortality worldwide: Sources, methods and major patterns in GLOBOCAN 2012", : International Journal of Cancer, 2012, vol. 136, No. 5, pp. E359-E386, 28 pages.

Finn et al., "Phase I study investigating everolimus combined with sorafenib in patients with advanced hepatocellular carcinoma", Journal of Hepatology, vol. 59, No. 6, pp. 1271-1277, 7 pages, 2013.

Fischer,et al., "Hematoxylin and eosin staining of tissue and cell sections", CSH Protocols, 2008, vol. 3, No. 5, 3 pages.

Gardino & Yaffe, "14-3-3 proteins as signaling integration points for cell cycle control and apoptosis", Seminars in Cell & Developmental Biology, 2011, vol. 22, No. 7, pp. 688-695, 18 pages.

Gohari et al., "An overview on saffron, phytochemicals, and medicinal properties", Pharmacognosy Reviews, vol. 7, No. 13, pp. 61-66, 7 pages, 2013.

Greenwell & Rahman, "Medicinal Plants: Their Use in Anticancer Treatment", International Journal of Pharmaceutical Sciences and Research, 2015, vol. 6, No. 10, pp. 4103-4112, 13 pages.

Hamza et al., "Molecular characterization of the grape seeds extract's effect against chemically induced liver cancer: In vivo and in vitro analyses", Scientific Reports, 2018, vol. 8 No. 1270, 16 pages.

Hanahan & Weinberg, "Hallmarks of Cancer: The Next Generation" Elsevier, Inc. Cell, 2011, vol. 144, No. 05, pp. 646-674, 29 pages.

Hassan et al., "Cape gooseberry (*Physalis peruviana*) juice as a modulator agent for hepatocellular carcinoma-linked apoptosis and cell cycle arrest", ELSEVIER, Science Direct, Biomedicine & Pharmacotherapy, 2017, vol. 94, pp. 1129-1137, 10 pages.

Hosseinzadeh et al., "Acute and Subacute Toxicity of Safranal, a Constituent of Saffron, in Mice and Rats", Iranian Journal of Pharmaceutical Research : IJPR, 2013, vol. 12, No. 1, pp. 93-99, 7 pages.

Hu et al., Common housekeeping proteins are upregulated in colorectal adenocarcinoma and hepatocellular carcinoma, making the total protein a better "housekeeper." Oncotarget, 2016, vol. 7, No. 41, p. 66679-66688, 10 pages.

Hübscher, "Histological assessment of the liver", Elsevier Ltd., Medicine, vol. 43, No. 10, pp. 568-572, 5 pages, 2015.

Juriková et al., "Ki67, PCNA, and MCM proteins: Markers of proliferation in the diagnosis of breast cancer", ELSEVIER, Acta Histochemica, 2016, vol. 118, No. 5, pp. 544-552, 9 pages.

Karafakoğlu et al., "Efficacy of safranal to cisplatin-induced nephrotoxicity", Portland Press, The Biochemical Journal Accepted Manuscript, 2017, vol. 474, No. 7, pp. 1195-1203, 27 pages.

Kesharwani et al., "Multifunctional approaches utilizing polymeric micelles to circumvent multidrug resistant tumors", ELSEVIER, Colloids and Surfaces B: Biointerfaces, 2019, vol. 173, pp. 581-590, 10 pages.

Kim & Kim, "Selection of optimal internal controls for gene expression profiling of liver disease", BioTechniques, 2003, vol. 35, No. 3, pp. 456-460, 3 pages.

Kmieć, "Cooperation of liver cells in health and disease", Advances in Anatomy, Embryology, and Cell Biology, 2001. vol. 161, III-XIII, 1-151, 1 page.

Lee et al., "Roles of Bcl-2 and caspase-9 and -3 in CD30-induced human eosinophil apoptosis", Science Direct, Journal of Microbiology, Immunology and Infection, 2017, vol. 50, No. 2, pp. 145-152, 8 pages.

Li et al., "PSAP induces a unique Apaf-1 and Smac-dependent mitochondrial apoptotic pathway independent of Bcl-2 family proteins", Biochim Biophys Acta (BBA)—Molecular Basis of Disease, 1832(3), 453-474, 2013.

Li et al., "Synthesis and biological evaluation of novel thiadiazole amides as potent Cdc25B and PTP1B inhibitors", ELSEVIER, Bioorganic & Medicinal Chemistry Letters, 2014, vol. 24, No. 17, pp. 4125-4128., 4 pages.

Liu et al., "Distinct pro-apoptotic properties of Zhejiang saffron against human lung cancer via a caspase-8-9-3 cascade", Research Article, Asian Pacific Journal of Cancer Prevention: APJCP, vol. 15, No. 15, pp. 6075-6080, 6 pages, 2014.

Liu et al., "Nitrogen-containing flavonoids as CDK1/Cyclin B inhibitors: Design, synthesis, and biological evaluation", ELSEVIER, Science Direct, Bioorganic & Medicinal Chemistry Letters, 2007, vol. 17, ,No. 1, pp. 278-281, 4 pages.

Llovet et al., "Sorafenib in Advanced Hepatocellular Carcinoma", SHARP Investigators Study Group, The New England Journal of Medicine, 2008, vol. 359, No. 4, pp. 378-390, 13 pages.

Los et al., "Activation and Caspase-mediated Inhibition of PARP: A Molecular Switch between Fibroblast Necrosis and Apoptosis in Death Receptor Signaling", Molecular Biology of the Cell, 2002, vol. 13, No. 3, pp. 978-988, 11 pages.

Lui, "Laboratory tests in liver failure", Clinical Assessment, Royal College of Anaesthetists CPD Matrix: 1A03, ELSEVIER, Anaesthesia & Intensive Care Medicine, 2017, vol. 19, No. 1, pp. 1-3, 3 pages.

Lv et al., "Agrin para-secreted by PDGF-activated human hepatic stellate cells promotes hepatocarcinogenesis in vitro and in vivo", Oncotarget, 2017, vol. 8, No. 62, pp. 105340-105355, 16 pages.

Machado et al., "Histopathological lesions, P-glycoprotein and PCNA expression in zebrafish (*Danio rerio*) liver after a single exposure to diethylnitrosamine", ELSEVIER, Science Direct, Environmental Toxicology and Pharmacology, 2014, vol. 38, No. 3, pp. 720-732, 13 pages.

Moreira et al., "Melatonin Activates Endoplasmic Reticulum Stress and Apoptosis in Rats with Diethylnitrosamine-Induced Hepatocarcinogenesis", Research Article, PLoS ONE, 2015, vol. 10, No. 12.

Mouri et al., "Combination therapy with carboplatin and paclitaxel for small cell lung cancer", ELSEVIER, Respiratory Investigation, 2019, vol. 57, No. 1, pp. 34-39, 6 pages.

Nair & Jacob, "A simple practical guide for dose conversion between animal and human", Journal of Basic and Clinical Pharmacy, Wolters Kluwer-Medknow, 2016, vol. 7, No. 2, pp. 27-31, 6 pages.

Nair & Staden, "Cell cycle modulatory effects of Amaryllidaceae alkaloids", ELSEVIER, Life Sciences, 2018, vol. 213, pp. 94-101, 8 pages.

Ozkececi et al., "Investigation of the effect of safranal and crocin pre-treatment on hepatic injury induced by infrarenal aortic occlusion". ELSEVIER, Science Direct, Biomedicine & Pharmacotherapy, 2016, vol. 83, pp. 160-166, 7 pages.

Pang & Lam, "Surgical management of hepatocellular carcinoma", World Journal of Hepatology, 2015, vol. 7, No. 2, pp. 245-252, 9 pages.

Prinsloo et al., "The use of plants containing genotoxic carcinogens as foods and medicine", ELSEVIER, Science Direct, Food and Chemical Toxicology, 2018, vol. 116, pp. 27-39. 13 pages.

Ramakrishna et al., "From Cirrhosis to Hepatocellular Carcinoma: New Molecular Insights on Inflammation and Cellular Senescence", Liver Cancer, Karger AG, Basel, 2013, vol. 2, pp. 367-383, 17 pages.

(56)         References Cited

PUBLICATIONS

Rana & Rana, "Review on Present Status and Future of Herbal Medicine", The Beats of Natural Sciences, 2014, vol. 1, No. 2, 8 pages.

Rates, "Plants as source of drugs", ELSEVIER, Toxicon, 2001, vol. 39, pp. 603-613, 11 pages.

Rezaee & Hosseinzadeh, "Safranal: From an Aromatic Natural Product to a Rewarding Pharmacological Agent", Iranian Journal of Basic Medical Sciences, 2013, vol. 16, No. 1, pp. 12-26, 15 pages.

Samarghandian et al., "Anti-tumor activity of safranal against neuroblastoma cells", Pharmacognosy Magazine, 2014, vol. 10(Suppl 2), pp. S419-S424, 7 pages.

Santos et al., "Animal models as a tool in hepatocellular carcinoma research: A Review", Tumor Biology, SAGE, 2017, vol. 39, No. 3, 20 pages.

Singhi et al., "Reticulin loss in benign fatty liver: an important diagnostic pitfall when considering a diagnosis of hepatocellular carcinoma", The American Journal of Surgical Pathology, 2012, vol. 36, No. 5, pp. 710-715, 6 pages.

Baig et al., "Cancer and Biotechnology: A Matchup that Should Never Slowdown", Chapter 3, Biotechnology and Production of Anti-Cancer Compounds, Springer International Publishing, 2017, pp. 73-97, 26 pages.

Srivastava et al., "Crocus sativus L.: A comprehensive review", Pharmacognosy Reviews, Publication of Pharmacognosy Network Worldwide, Medknow Publications, 2010, vol. 4, No. 8, pp. 200-208, 11 pages.

Subramaniam, et al., "Potential role of signal transducer and activator of transcription (STAT)3 signaling pathway in inflammation, survival, proliferation and invasion of hepatocellular carcinoma", ELSEVIER, Biochimica et Biophysica Acta (BBA)—Reviews on Cancer, 2013, vol. 1835, No. 1, pp. 46-60, 15 pages.

Tadmouri & Al-Sharhan, "Cancers in the United Arab Emirates", Genetic Disorders in the Arab World: United Arab Emirates, 2004, pp. 59-61, 3 pages.

Wang et al., "Proliferating cell nuclear antigen promotes cell proliferation and tumorigenesis by up-regulating STAT3 in non-small cell lung cancer", ELSEVIER, Biomedicine & Pharmacotherapy, 2018, vol. 104, pp. 595-602, 8 pages.

Wen et al., "Collapsed Reticular Network and its Possible Mechanism during the Initiation and/or Progression of Hepatic Fibrosis", Scientific Reports, vol. 6, No. 35426,11 pages, 2016.

Xie et al., "miR-152 inhibits proliferation of human endometrial cancer cells via inducing G2/M phase arrest by suppressing CDC25B expression", ELSEVIER, Biomedicine & Pharmacotherapy, 2018, vol. 99, pp. 299-305, 7 pages.

Yao et al., "Diagnostic Value of Immunohistochemical Staining of GP73, GPC3, DCP, CD34, CD31, and Reticulin Staining in Hepatocellular Carcinoma", Journal of Histochemistry and Cytochemistry, 2013, vol. 61, No. 9, pp. 639-648, 10 pages.

Yinti et al., "Analysis of reticulin fiber pattern in lymph nodes with metastasis from oral squamous cell carcinoma", Dental Hypotheses, Wolters Kluwer-Medknow, 2015, vol. 6, No. 3, pp. 104-108, 5 pages.

Zhang et al., "The activation of p38 and JNK by ROS, contribute to OLO-2-mediated intrinsic apoptosis in human hepatocellular carcinoma cells", ELSEVIER, Food and Chemical Toxicology, 2014, vol. 63, pp. 38-47, 10 pages.

Zhou et al., "Systematic Review with Network Meta-Analysis: Antidiabetic Medication and Risk of Hepatocellular Carcinoma". Scientific Reports, 2016, vol. 6, 10 pages.

Amin et al., "Evasion of anti-growth signaling: A key step in tumorigenesis and potential target for treatment and prophylaxis by natural compounds". ELSEVIER, Seminars in Cancer Biology, 2015, vol. 35, pp. S55-S77, 23 pages.

Yaswen et al., "Therapeutic targeting of replicative immortality" ELSEVIER, Seminars in Cancer Biology, 2015, vol. 35, pp. S104-S128, 25 pages.

Samadi et al., "A multi-targeted approach to suppress tumor-promoting inflammation". ELSEVIER, Seminars in Cancer Biology, 2015, vol. 35, pp S151-S184, 34 pages.

Amin & Lowe, "Plant-Based Anticancer Drug Development: Advancements and Hurdles", Journal of Gastrointestinal & Digestive System, 2012, vol. 2, No. 5, 2 pages.

Block et al., "Designing a broad-spectrum integrative approach for cancer prevention and treatment", ELSEVIER, Seminars in Cancer Biology, 2015, vol. 35, pp. S276-S304, 29 pages.

Al-Hrout et al., "Cancer and Biotechnology: A Matchup that Should Never Slowdown", Chapter 3, Biotechnology and Production of Anti-Cancer Compounds, Springer International Publishing, 2017, pp. 73-97, 26 pages.

Amin et al., "Defective Autophagosome Formation in p53-Null Colorectal Cancer Reinforces Crocin-Induced Apoptosis", International Journal of Molecular Sciences, 2015, vol. 16, pp. 1544-1561, 18 pages.

Hamza et al., "Melissa officinalis Protects against Doxorubicin-Induced Cardiotoxicity in Rats and Potentiates Its Anticancer Activity on MCF-7 Cells", PLOSone, 2016, 25 pages.

Al-Akhras et al., "Introducing Cichorium Pumilum as a Potential Therapeutical Agent Against Drug-Induced Benign Breast Tumor in Rats", Informa Healthcare USA, Inc., Electromagnetic Biology and Medicine, 2012, 12 pages.

Amin et al., "Neural network assessment of herbal protection against chemotherapeutic-induced reproductive toxicity", BioMed Central, Theoretical Biology and Medical Modelling, 2012, vol. 9, No. 1, 15 pages.

Amin, "Protective Effect of Green Algae Against 7,12-Dimethylbenzanthracene (DMBA)-Induced Breast Cancer Rats", International Journal of Cancer Research, 2009, vol. 5, No. 1, pp. 12-24, 14 pages.

Al-Akhras et al., "In Vitro Studies on the Effect of Phototoxicity of A New Photosensitizer Extracted from Flowers and Aerial Parts of Cichorium pumilum", American Journal of Pharmacology and Toxicology, 2007, vol. 2, No. 2, pp. 39-45, 8 pages.

Liu et al., "Molecular Serum Markers of Liver Fibrosis", Biomarker Insights, Libertas Academica Freedom to Research, 2012, vol. 7, pp. 105-117, 13 pages.

Ferlay, J. et al., "Cancer incidence and mortality worldwide: Sources, methods and major patterns in GLOBOCAN 2012", International Journal of Cancer, 2015, vol. 136, Issue 5, 2014, pages E359-E386, 28 pages.

Sherman, "Hepatocellular Carcinoma: Epidemiology, Surveillance, and Diagnosis", Seminar in Liver Disease, Department of Medicine, University of Toronto and University Health Network, Toronto, Canada, Thieme Medical Publishers, Inc., 2010, vol. 30, No. 1, 14 pages.

Nahon, et al., "Hepatic iron overload and risk of hepatocellular carcinoma in cirrhosis", Elsevier Masson, ScienceDirect, US National Library of Medicine, Gastroenterologie Clinique et. Biologique, 2009, vol. 34, Issue 1, pp. 1-7, 7 pages.

Starley et al., "Nonalcoholic fatty liver disease and hepatocellular carcinoma: a weighty connection", Hepatology, vol. 51, No. 5, 2010, pp. 1820-1832, 13 pages.

Kinghorn et al., "Discovery of Natural Product Anticancer Agents from Biodiverse Organisms", Curr. Opin. Drug Discov. Devel., 2009, vol. 12, pp. 189-196, 12 pages.

Newman, D. J. & Cragg, G. M., "Natural products as sources of new drugs from 1981 to 2014", Journal of Natural Products, 2016, vol. 79, pp. 629-661, 33 pages.

Greenlee, "Natural products for cancer prevention" Semin. Oncol. Nurs., 2012, vol. 28, pp. 29-44, 16 pages.

Bachrach, "Contribution of selected medicinal plants for cancer prevention and therapy", Acta Facultatis Medicae Naissensis, 2012, vol. 29, No. 3, 7 pages.

Amin et al., "Saffron-based crocin prevents early lesions of liver cancer: In vivo, In vitro and network Analyses", Recent Pat Anti-cancer Drug Discovery, 2016, vol. 11, pp. 121-133, 13 pages.

Amin et al., "Saffron: A potential candidate for a novel anticancer drug against hepatocellular carcinoma", Hepatology, 2011, vol. 54, pp. 857-867, 11 pages.

(56)          References Cited

PUBLICATIONS

Samarghandian, et al., "Anti-tumor activity of safranal against neuroblastoma cells", Pharmacognosy Magazine, 2014, vol. 10, pp. S419-S424, 11 pages.

Samarghandian & Shabestari, "DNA fragmentation and apoptosis induced by safranal in human prostate cancer cell ine", Indian Journal of Urology, 2013, vol. 29, pp. 177-183, 13 pages.

Escribano, et al., "Crocin, safranal and picrocrocin from saffron (Crocus sativus L.) inhibit the growth of human cancer cells in vitro", Cancer Letters, ELSEVIER, 1996, vol. 100, pp. 23-30, 8 pages.

Assimopoulou et al., "Radical Scavenging Activity of Crocus sativus L. Extract and its Bioactive Constituents", Phytotherapy Research, 2005, Voume 19, pp. 997-1000, 4 pages.

Samarghandian & Boskabady, "Caspase-dependent pathway in apoptosis induced by Safranal in alveolar human lung cancer cell line", Research in Pharmaceutical Sciences, 2012, vol. 7, 1 page.

Sharma et al., "Histone H2AX phosphorylation: a marker for DNA damage", 2012, Methods in Molecular Biology, vol. 920, 613-626, 15 pages.

Warmerdam & Kanaar, "Dealing with DNA damage: Relationships between checkpoint and repair pathways", Mutation Research—Reviews in Mutation Research, 2010, vol. 704, pp. 2-11, 10 pages.

Zhang et al., "Safranal inhibits the migration and invasion of human oral squamous cell carcinoma cells by overcoming epithelial-mesenchymal transition", Biomedical Research, 2017, vol. 28, pp. 817-821, 5 pages.

Samarghandian & Borji, "Anticarcinogenic effect of saffron (Crocus sativus L.) and its ingredients", Pharmacognosy Research, 2014, vol. 6, pp. 99-107, 15 pages.

Milajerdi et al., "The toxicity of saffron (Crocus sativus L.) and its constituents against normal and cancer cells", Journal of Nutrion & Intermediary Metabolism, 2016, vol. 3, pp. 23-32, 39 pages.

Nigam et al., "Targeting mortalin by embelin causes activation of tumor suppressor p53 and deactivation of metastatic signaling in human breast cancer cells", PLoS One, 2015, vol. 10, 16 pages.

Hu et al., :Lycorine is a novel inhibitor of the growth and metastasis of hormone-refractory prostate cancer, Oncotarget, Advance Publications, 2015, vol. 6, 15 pages.

Wang et al., "Baicalein induces apoptosis and autophagy via endoplasmic reticulum stress in hepatocellular carcinoma cells", Biomed Research International, 2014, vol. 2014, 14 pages.

Contour-Galcera et al., "What's new on CDC25 phosphatase inhibitors", Pharmacology and Therapeutics, 2007, vol. 115, 12 pages.

Lund et al., "Inhibition of CDC25B phosphatase through disruption of protein-protein interaction". ACS Chemical Biology, 2015, vol. 10, pp. 390-394, 5 pages.

Lavecchia et al., "CDC25 phosphatase inhibitors: an update", Mini-Reviewes in Medicinal Chemistry, 2012; vol. 12, pp. 62-73, 13 pages.

Lavecchia et al., "Cdc25B phosphatase inhibitors in cancer therapy: latest developments, trends and medicinal chemistry perspective", Anti-cancer Agents Medicinal Chemistry, 2008, vol. 8, pp. 843-856, 15 pages.

Ham et al., "Studies on menadione as an inhibitor of the cdc25 phosphatase", Bioorganic Chemistry, 1997, vol. 25, pp. 33-36, 4 pages.

Tamura et al., "Cdc25 inhibition and cell cycle arrest by a synthetic thioalkyl vitamin K analogue", Cancer Research, 2000, vol. 60, pp. 317-1325, 10 pages.

Wu et al., "UCN-01 induces S and G2/M cell cycle arrest through thep53/p21(waf1) or CHK2/CDC25C pathways and can suppress invasion in human hepatoma cell lines", 2013, vol. 13, No. 167, 10 pages.

Fragkos et al., "H2AX Is required for cell cycle arrest via the p53/p21 pathway", Molecullar and Cellular Biology, 2009, vol. 29, No. 10, pp. 2828-2840, 13 pages.

Das et al., "PARP1-TDP1 coupling for the repair of topoisomerase I-induced DNA damage", Nucleic Acids Research, 2014, vol. 42, No. 7, pp. 4435-4449, 15 pages.

Dexheimer et al., "Tyrosyl-DNA phosphodiesterase as a target for anticancer therapy", Anticancer Agents Med Chem., 2008, vol. 8, No. 4, pp. 381-389, 17 pages.

Pommier et al., "DNA topoisomerases and their poisoning by anticancer and antibacterial drugs", Chemistry and Biology Review, 2010, vol. 17, pp. 421-433, 13 pages.

Huang et al., "Tyrosyl-DNA Phosphodiesterase 1 (Tdp1) inhibitors", Expert Opin. Ther. Pat., 2011, vol. 21, No. 9, pp. 1285-1292, 10 pages.

Miller et al., "Human HDAC1 and HDAC2 function in the DNA-damage response to promote DNA nonhomologous endjoining". Nat. Struct. Mol. Biol., 2010, vol. 17, No. 9, pp. 1144-1151, 20 pages.

Roos & Kaina, "DNA damage-induced cell death by apoptosis", ELSEVIER, Trends in Molecular Medicine, 2006, vol. 12, No. 9, pp. 440-450, 11 pages.

McIlwain et al., "Caspase functions in cell death and disease", . Cold Spring Harbor Perspective in Biology, 2013, vol. 5, 28 pages.

Hamsa & Kuttan, "Harmine activates intrinsic and extrinsic pathways of apoptosis in B16F-10 melanoma". Chinese Medicine, 2011, vol. 6, No. 11, 8 pages.

Kang et al., "Inhibition of EGFR signaling augments oridonin-induced apoptosis in human laryngeal cancer cells via enhancing oxidative stress coincident with activation of both the intrinsic and extrinsic apoptotic pathways", Cancer Letters, ELSEVIER, 2010, vol. 294, pp. 147-158, 12 pages.

Hsieh et al., "Antcin B and its ester derivative from Antrodia camphorata induce apoptosis in hepatocellular carcinoma cells involves enhancing oxidative stress coincident with activation of intrinsic and extrinsic apoptotic pathway", Journal of Agricultural and Food Chemistry, 2011, vol. 59, pp. 10943-10954, 12 pages.

Momoi, "Caspases involved in ER stress-mediated cell death", Journal of Chemical Neuroanatomy, 2004, vol. 28, pp. 101-105, 5 pages.

Winter et al., "Involvement of extrinsic and intrinsic apoptotic pathways together with endoplasmic reticulum stress in cell death induced by naphthylchalcones in a leukemic cell line: Advantages of multi-target action", ELSEVIER, Toxicology in Vitro, 2014, vol. 28, pp. 769-777, 9 pages.

Pickart & Eddins, "Ubiquitin: structures, functions, mechanisms", ELSEVIER, Biochimica et Biophysica Acta—Molecular Cell Research, 2004, vol. 1695, pp. 55-72, 18 pages.

Tabas & Ron, "Integrating the mechanisms of apoptosis induced by endoplasmic reticulum stress", . Nat. Cell Biol., 2011, vol. 13, No. 3, pp. 184-190, 17 pages.

Pagliarini et al., "Downregulation of E2F1 during ER stress is required to induce apoptosis", Journal of Cell Science, 2015, vol. 128, pp. 1166-1179, 14 pages.

Lee, "GRP78 induction in cancer: therapeutic and prognostic implications", American Association for Cancer Research , 2007, pp. 3496-3499, 5 pages.

Rahmani et al., "The kinase inhibitor sorafenib induces cell death through a process involving induction of endoplasmic reticulum stress", Molecullar and Cellular Biology, 2007, vol. 27, No. 15, pp. 5499-5513, 15 pages.

Han et al., "Endoplasmic reticulum stress inhibits cell cycle progression via induction of p27 in melanoma cells". ELSEVIER, Cellular Signalling, 2013, vol. 25, pp. 144-149. 6 pages.

Brewer et al., "Mammalian unfolded protein response inhibits cyclin D1 translation and cell-cycle progression", Proc. Natl. Acad. Sci. USA , 1999, vol. 96, pp. 8505-8510, 6 pages.

Stephen M. Berge, "Pharmaceutical Salts", Article, 1997, 1-19, vol. 66, No. 1, Journal of Pharmaceutical Sciences.

* cited by examiner

Safranal 12 hi down | 12 hi up | 24 hi down | 24 hi up

| | | | |
|---|---|---|---|
| FLRT1 | ACTL8 | SLCO2A1 | RP11-498C9.12 |
| SPRR2D | MAP1A | FLRT1 | HSPA1B |
| SLCO2A3 | MYB | RP11-284F21.11 | RP11-227G15.12 |
| DDIT3 | FAM111B | TNC | SNORD38-1 |
| LURAP1L | PLA2G12AP1 | CCL22 | RP11-160E2.6 |
| ITGAX | SGIP1 | SLC5A1 | AKR1B10 |
| KLHDC7B | CTD-2589H19.6 | SSPO | TREML3P |
| RP11-284F21.11 | MCM4 | IL2RB | SNORD38-2 |
| ADTRP | AS3B16 | CYP4F2 | RP11-93B14.6 |
| MYO7B | CTD-212488.2 | MMP1 | CTD-2589H19.6 |
| CLDN1 | PK55 | KRT86 | RP11-461A8.4 |
| IL2RB | HSPH1 | SPRR2D | LA16c-431H6.6 |
| BEST1 | KL8 | TNFSF18 | CTD-212488.2 |
| SPX | HSPA8 | TCP11L2 | RP11-50B39.2 |
| LEMD1 | RP11-135F9.4 | CLIC3 | PRR19 |
| LINC00669 | RP11-133K1.11 | MYO7B | HSPA1B |
| MMP1 | RP11-44F14.10 | DAPP1 | RP11-151N17.1 |
| TSLP | FEN1 | KLHDC7B | PODNL1 |
| SSPO | AC006946.15 | ABALON | RP11-350I20.5 |
| PTGDS | LINC00852 | SPOCK3 | LRRN4CL |
| RP11-1094H24 | EMC3-AS1 | COL15A1 | HSPA1B |
| VGF | AXIN2 | PTGS1 | HSPE1 |
| ANKFN1 | NID2 | CLDN1 | ATP5G1P4 |
| SPRR1B | DHFR | TM4SF1 | MIR3153 |
| CYP11A1 | HSPA1B | GCOM1 | AC063976.7 |
| ASIC4 | CHORDC1 | RORC | SNORA28 |
| SERPINE1 | CH507-154B10.1 | ITGAX | MYLK2 |
| KRT86 | DOK3 | PLAU | HMGN1P2 |
| DAPP1 | MYLK2 | SPRR1B | ATP6V0C |
| RP11-88I21.1 | RCBTB2 | RP11-875O11.3 | RP11-316M1.3 |
| NDRG1 | RP11-461A8.4 | FBLN2 | THUMPD3-AS1 |
| RP5-1198O2D.4 | KCNK3 | TNFRSF9 | ACTL8 |
| MUC12 | ACTRT3 | DIRAS3 | SARNP |
| DIRAS3 | SKIDA1 | HSPG2 | CNO1-IT1 |
| QPCT | RP11-121C6.5 | TRPV6 | ZNF670 |
| FBLN2 | LINC00342 | PSAPL1 | HSPA1B |
| LINC01537 | RP11-127B20.2 | ANKRD22 | RP11-223P11.3 |
| CPN1 | PI3W | ENPP2 | SNHG14 |
| ADRA1B | PRR19 | UPK3A | RP11-383C5.5 |
| TE1 | TMEM165 | GJB4 | RP11-886P16.10 |
| SLC5A1 | PRR22 | DOK1 | ADM5 |
| IL20RB | CH507-154B10.2 | ADRA1B | LINC00852 |
| LINC00850 | RP11-10O17.1 | SPX | XXyac-YRM2039.3 |
| CCL22 | HNRNPM | UPG | RP11-121C6.5 |
| LAT2 | DHX9 | NCAM1 | GTSE1-AS1 |
| PRPH | AC099850.1 | DMBT1 | RP5-967N21.11 |
| UPP1 | MCM5 | ADGRF1 | CTC-548K16.1 |
| WNT4 | RP5-967N21.11 | TMC1 | RP11-122M14.1 |
| SEAN1 | DGCR8 | RP11-342D14.1 | RP11-500C11.3 |
| C16orf96 | RP3-467L1.6 | LINC01366 | AC099850.1 |

Log2
(Gene expression)

-6　　　　4

FIG. 6A a versus PBS, b versus HCC; *P < 0.05, P < 0.01, *P < 0.001 a versus PBS, b versus HCC; P < 0.01, *P < 0.001 a versus PBS, b versus HCC; *P < 0.05, ***P < 0.001 a versus PBS, b versus HCC; *P < 0.05, P < 0.01, *P <
0.001 b versus HCC; *P < 0.05          a versus PBS, b versus HCC; *P < 0.05, ***P < 0.001 a versus PBS, b versus HCC; *P < 0.05 a versus PBS, b versus HCC; *P < 0.05, **P < 0.01 a versus PBS, b versus HCC; *P < 0.05, P < 0.01, *P < 0.001 a versus PBS, b versus HCC, c versus HCC + SB; *P < 0.05, P < 0.01, *P < 0.001

| Species | Reference body weight (kg) | Working weight range (kg) | Body surface area (m²) | To convert dose in mg/kg to dose in mg/m² multiply by K$_m$ | To convert animal dose in mg/kg to HED in mg/kg, either | |
|---|---|---|---|---|---|---|
| | | | | | Divide animal dose by | Multiply animal dose by |
| Human | 60 | - | 1.62 | 37 | - | - |
| Mouse | 0.02 | 0.011-0.034 | 0.007 | 3 | 12.3 | 0.081 |
| Hamster | 0.08 | 0.047-0.157 | 0.016 | 5 | 7.4 | 0.135 |
| Rat | 0.15 | 0.08-0.27 | 0.025 | 6 | 6.2 | 0.162 |
| Ferret | 0.30 | 0.16-0.54 | 0.043 | 7 | 5.3 | 0.189 |
| Guinea pig | 0.40 | 0.208-0.700 | 0.05 | 8 | 4.6 | 0.216 |
| Rabbit | 1.8 | 0.90-3.0 | 0.15 | 12 | 3.1 | 0.324 |
| Dog | 10 | 5-17 | 0.50 | 20 | 1.8 | 0.541 |
| Monkeys (rhesus) | 3 | 1.4-4.9 | 0.25 | 12 | 3.1 | 0.324 |
| Marmoset | 0.35 | 0.14-0.72 | 0.06 | 6 | 6.2 | 0.162 |
| Squirrel monkey | 0.60 | 0.29-0.97 | 0.09 | 7 | 5.3 | 0.189 |
| Baboon | 12 | 7-23 | 0.60 | 20 | 1.8 | 0.541 |
| Micro pig | 20 | 10-33 | 0.74 | 27 | 1.4 | 0.730 |
| Mini pig | 40 | 25-64 | 1.14 | 35 | 1.1 | 0.946 |

FIG. 22

COMBINATION THERAPY FOR CANCER

CROSS-REFERENCE TO RELATED APPLICATION

This application is continuation of U.S. patent application Ser. No. 16/272,426, filed on Feb. 11, 2019, the entire disclosure of which is incorporated herein by reference.

TECHNICAL FIELD

The present invention relates to therapeutic formulations and methods for treating liver cancer including safranal and optionally topoisomerase-1 inhibitors.

BACKGROUND

Despite all efforts, more people are diagnosed with hepatocellular carcinoma (HCC); the most common type of primary liver cancer and the second leading cause of cancer-related death worldwide [1]. Multiple risk factors contribute to HCC development including chronic hepatitis (B and C) infection that accounts for 70%-90% of HCC cases by providing a permissive environment for HCC development [2]. Other HCC risk factors include alcoholism, non-alcohol fatty liver disease, iron overload, and environmental carcinogens [3,4]. Early stages of HCC show no symptoms, thus most patients are diagnosed at advanced stages. In addition, HCC exhibits a high rate of recurrence after resection or ablation; and is considerably resistant to cytotoxic chemotherapy, with a very limited number of available treatments. Thus, alternative therapeutics are well justified and are desperately needed to treat HCC.

Chemotherapy is the most common treatment of cancer patients. Taxanes (such as paclitaxel) are among the most potent chemotherapeutic agents used in the treatment of multiple solid tumors. The occurrence of resistance does however limit treatment options and represent a main challenge for clinicians (Fanale et al., 2015). Breast, lung and ovarian cancers are all, in fact, resistant (also known as Multi Drug Resistant "MDR" tumors) to paclitaxel therapy (Kesharwani et al., 2019). Small cell lung cancer (SCLC), a common neuroendocrine tumor, accounts for about 20% of all cases of lung cancer. As SCLC shows significant sensitivity to chemotherapy, a combination of the paclitaxel with platinum-based therapy "carboplatin" was found to be effective and feasible for the treatment of relapsed SCLC (Mouri et al., 2019). Similarly, in the highly heterogeneous epithelial ovarian cancer (EOC) that accounts for most of diagnosed ovarian cancers, studies strongly indicate that metformin is a valuable adjuvant therapy for cancer, improving treatment efficacy and lower doses of chemotherapy agents in EOC. Metformin has been shown to block proliferation in paclitaxel-resistant and in cisplatin-resistant cell lines and to enhance the sensitivity of resistant cell lines to conventional drugs.

By the same token, the heterogeneity of hepatocellular carcinoma (HCC) cells that accounts for intratumor heterogeneity in 87% of HCC cases, the poor response of HCC to systemic chemotherapy and its extreme chemoresistance, currently instigate an intense search for agents that could overcome the MDR phenotype. However, for a prototypical therapy-resistant tumor like HCC, MDR continues to be a major hurdle that slows down the therapeutic efficacy of all available antitumoral agents. Thus, overcoming MDR is a current area of urgent clinical and preclinical research.

Sorafenib is the first anti-HCC drug approved by the U.S. Food and Drug Administration. It is a multikinase inhibitor that blocks tumor cells proliferation and angiogenesis. Although sorafenib is successful treating early and mid HCC lesions, it is not efficient in advanced HCC cases. The common side effects of sorafenib are skin toxicity, diarrhea, hypertension, and bleeding. In addition, combining drugs with other molecular or immunotherapies to overcome such drawbacks is emerging as an area of utmost importance in research. Unfortunately, most of the attempted sorafenib's combination therapies have not proven effective to say the least. Therefore, there is an urgent need in clinical trials for sorafenib to be used in combination with different anticancer drug candidates.

Natural products have long been a part of folk medicine and have been playing an instrumental role in the development of anti-cancer drugs [5]. Thanks to their nontoxicity and low-to-non associated side effects, 40% of FDA-approved therapeutic agents are natural-based components or their derivatives [6]. Considering their great efficacy and low toxicity, natural products have been extensively studied and introduced as a chemopreventive therapy for many diseases including cancer [7]. Medicinal plants have been suggested for cancer prevention and therapy for several reasons; they contain nutritional and anti-tumor compounds, are able to delay or prevent cancer onset, can boost the physiological status and the immune system, and most importantly, they represent a great alternative and/or adjuvant option to conventional cancer treatments by alleviating or even averting their side effects [8].

Saffron (the stigmas of the flower of *Crocus sativus*), is increasingly gaining attention as it contains many bioactive molecules with health promoting properties; including crocin, crocetin, picrocrocin, and safranal, The structure of the safranal molecule is represented in FIG. 1A. Previous studies have reported the anti-cancer activity of saffron and its derivatives against a wide range of cancers [9-12]. While saffron's derivatives have been reported to inhibit the growth of HeLa cells [13], safranal has specifically been shown to exert potent anti-inflammatory, antioxidant and anti-cancer properties [14] and was found to induce apoptosis in both alveolar human lung cancer A549 [15], and human prostate cancer PC-3 cell lines [12]. Despite all its anti-tumor activities, the mechanism through which safranal exerts its anti-cancer effect is yet to be fully understood.

Hence, it would be advantageous to understand the mechanism through which safranal exerts anti-cancer effects so it may be developed into an effective treatment for liver and other cancer types.

SUMMARY

In accordance with a first aspect of the invention, there is provided a method of treating, suppressing, or reducing the severity of a liver cancer in a subject. The method includes administering to the subject a therapeutically effective amount of a composition including: safranal or a pharmaceutically acceptable pro-drug thereof, and a pharmaceutically acceptable carrier. The liver cancer may be a hepatocellular carcinoma (HCC), a fibrolamellar HCC, a cholangiocarcinoma, an angiosarcoma, a metastatic liver cancer, and combinations thereof. In example embodiments, the therapeutically effective amount may be administered orally, parenterally, or to a hepatic artery. In a representative embodiment, the amount of the safranal or of the pharmaceutically acceptable pro-drug thereof is from about 10 mg/day to about 1000 mg/day per kg body weight of the subject. In another embodiment, the amount of the safranal or of the pharmaceutically acceptable pro-drug thereof is from about 200 mg/day to about 750 mg/day per kg body weight of the subject. In a further embodiment, the amount of the safranal or of the pharmaceutically acceptable pro-drug thereof is from about 250 mg/day to about 500 mg/day per kg body weight of the subject. In a representative embodiment, the amount of the safranal or of the pharmaceutically acceptable pro-drug thereof is sufficient to increase the cytotoxic effect of aTOP1 inhibitor on cancer cells. Example pro-drugs include safranal salts, hydrates, hemiacetals, acetals, thioacetals, silylethers, tautomers, and isomers. In an additional embodiment, the method further includes administering a second therapeutic agent selected from the group consisting of carboplatin; cisplatin; methotrexate; fluorouracil; gemcitabine; goserelin; leuprolide; tamoxifen; taxanes; aldesleukin; interleukin-2; etoposide; interferon alfa; tretinoin; bleomycin; dactinomycin; daunorubicin; doxorubicin; mitomycin; vinblastine; vincristine, irinotecan, topotecan, camptothecin, lamellarin D, and combinations thereof.

In accordance with a second aspect of the invention, there is provided a method of treating, suppressing, or reducing the severity of a liver cancer in a subject. The method includes: administering to the subject a first amount of safranal or a pharmaceutically acceptable pro-drug thereof, and administering to the subject a second amount of a TOP1 inhibitor. The TOP1 may be selected from the group consisting of irinotecan, topotecan, camptothecin, lamellarin D, and combinations thereof. In one embodiment, the safranal or its pro-drug and the TOP1 inhibitor are compounded together in one composition including both compounds. In another embodiment, the safranal or its pro-drug and the TOP1 inhibitor are administered separately in separate pharmaceutical compositions. The safranal or its pro-drug and the TOP1 inhibitor may administered in a sequential manner. In an embodiment, the safranal or its pro-drug is administered first to sensitize the cancer cells prior to exposure to the TOP1 inhibitor, and the TOP1 inhibitor is administered second. Example safranal pro-drugs include safranal salts, hydrates, hemiacetals, acetals, thioacetals, silylethers, tautomers, isomers, and combinations thereof. The liver cancer may be a hepatocellular carcinoma, fibrolamellar HCC, cholangiocarcinoma, angiosarcoma, a metastatic liver cancer, and combinations thereof.

In accordance with a third aspect of the invention, there is provided a therapeutic combination of drugs for the treatment of a liver cancer, the combination including: safranal or a pharmaceutically acceptable pro-drug thereof, and a TOP1 inhibitor. The TOP1 inhibitor may be selected from the group consisting of irinotecan, topotecan, camptothecin, lamellarin D, and combinations thereof. The pro-drug may be selected from the group consisting of a safranal salt, hydrate, hemiacetal, acetal, thioacetal, silylether, tautomer, isomer, and combinations thereof. In an embodiment, the safranal and the TOP1 inhibitor are compounded together in a same unitary pharmaceutical composition including both compounds. In another embodiment, the safranal and the TOP1 inhibitor are in separate pharmaceutical compositions. In representative embodiments, the amount of the TOP1 inhibitor is 0.1:1 to 10:1 by weight with respect to the content of the safranal of the combination.

BRIEF DESCRIPTION OF THE DRAWINGS

The invention can be better understood with reference to the following figures and description. The components in the figures are not necessarily to scale and are not intended to accurately represent molecules, cells, cell organelles, tissues, or their interactions, emphasis instead being placed upon illustrating the principles of the invention.

FIGS. 1A-1D establish that safranal inhibits growth and survival of HepG2 cells.

Figures 1A, 1B:
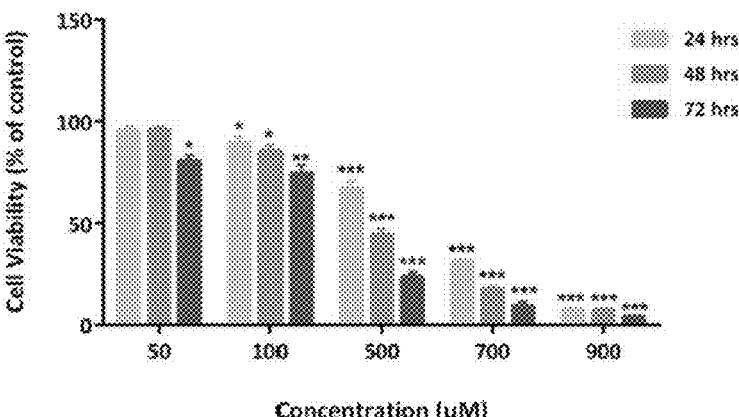

FIG. 1A represents the chemical structure of safranal.

FIG. 1B provides the cell viability of HepG2 cells after treatment with different concentrations of safranal for 24, 48 and 72 hour timeframes.

Figure 1C:
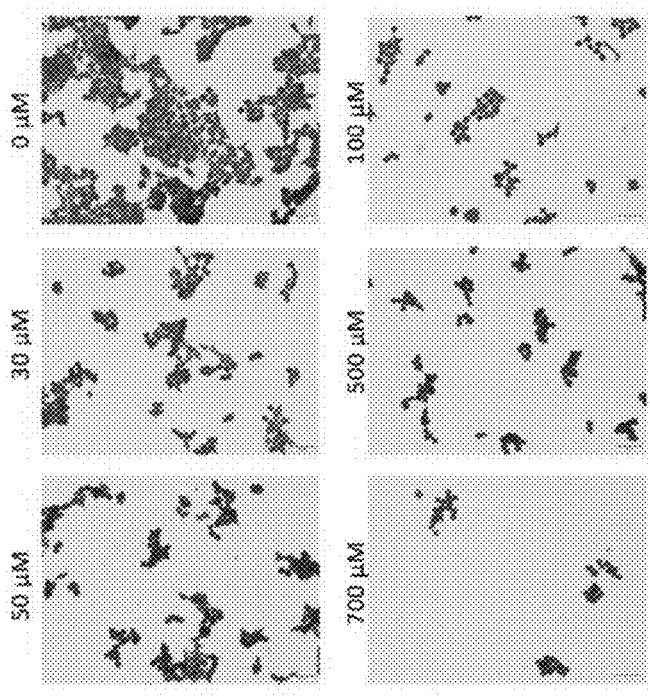

FIG. 1C. Assessment of morphological changes of safranal-treated HepG2 cells (24 hours). Cells were fixed and stained with crystal violet.

Figure 1D:
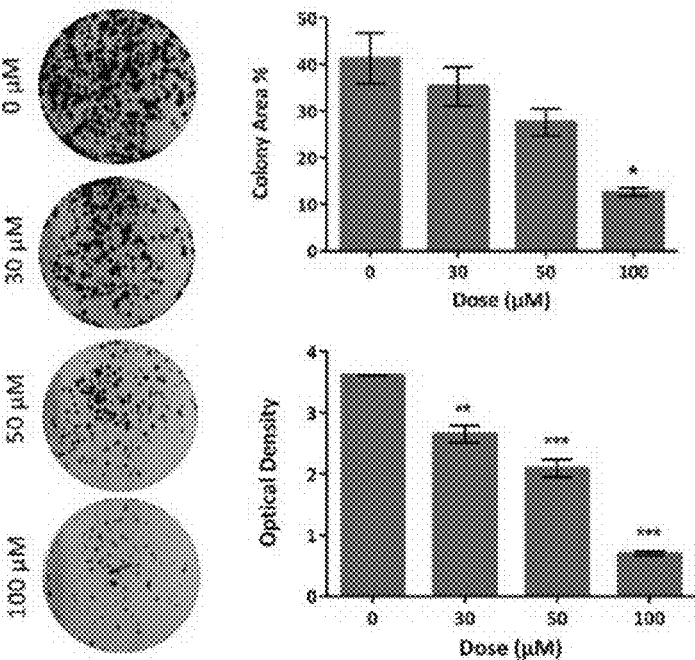

FIG. 1D provides representative images of a colony formation assay of HepG2 cells treated with different concentrations of safranal for a 24 hour timeframe.

Figure 2A:
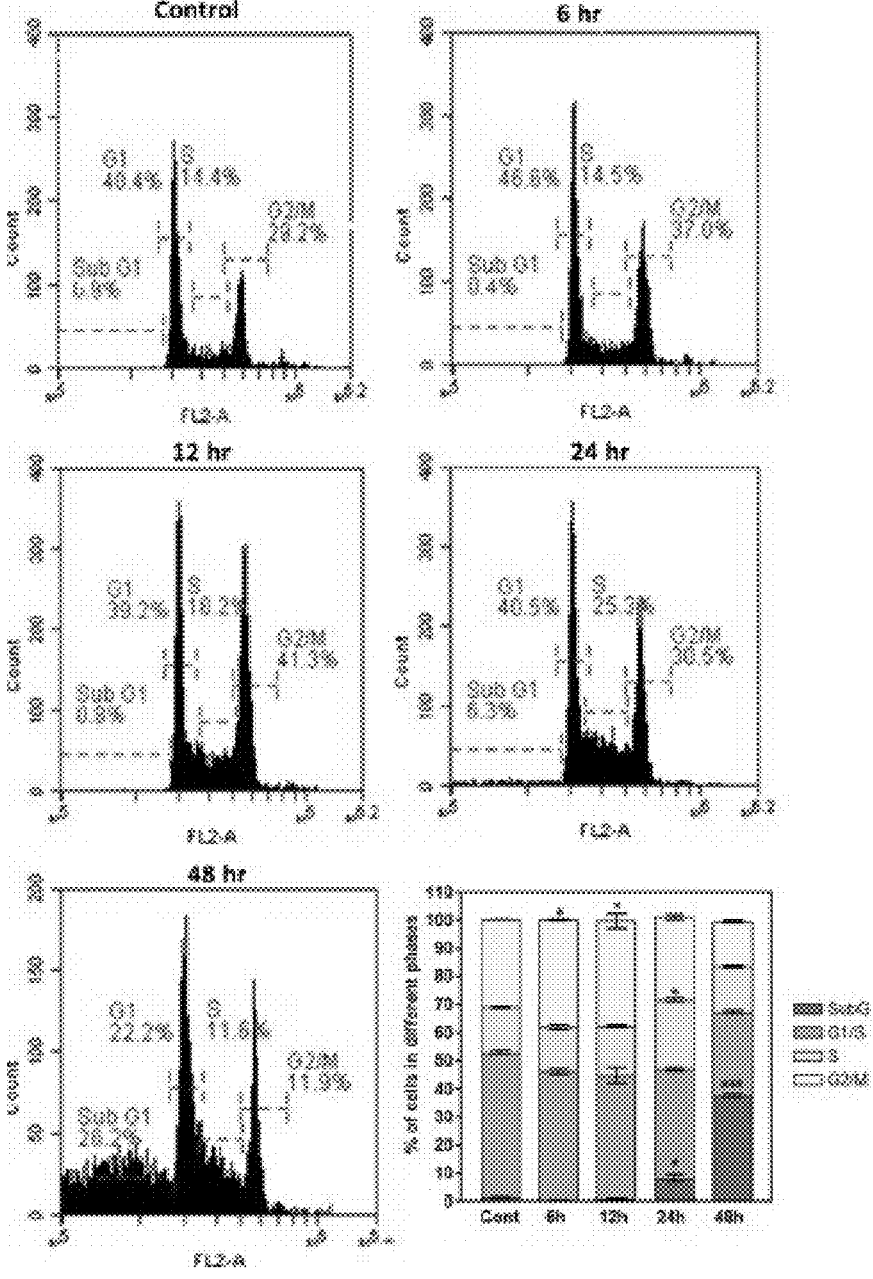
Figure 2B:
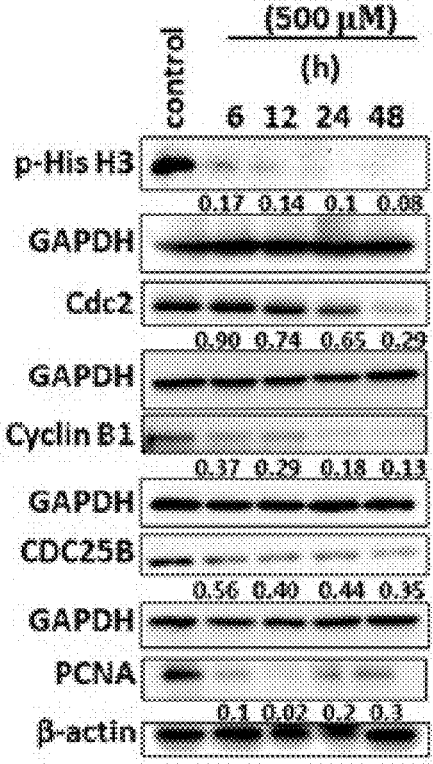
Figure 2C:
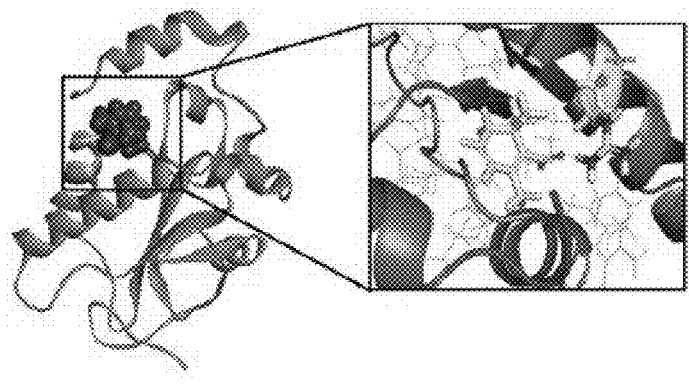

FIGS. 2A-2C establish that safranal arrests HepG2 cells at G2/M and S Phase and affects cell cycle regulators.

FIG. 2A represents cell cycle progression of HepG2 cells after treatment with safranal at a dose of 500 μM over a period of 48 hours; and quantitative distribution of HepG2 cells in different phases of the cell cycle at different time intervals. Statistical analysis was carried out by student's t-test using GraphPad Prism software and $p < 0.05$ was considered as statistically significant. $*p < 0.05$ and $***p < 0.01$.

FIG. 2B provides a western blot analysis of cell cycle regulatory proteins in HepG2 cells post treatment with safranal at a dose of 500 μM. Each band intensity was quantified using ImageJ, normalized relative to their respective loading control bands. Values are expressed as ratio of untreated control. Western blot images of FIG. 2B have been cropped for clarity.

FIG. 2C illustrates best docked poses of safranal within the human CDC25B binding site.

Figure 3A:
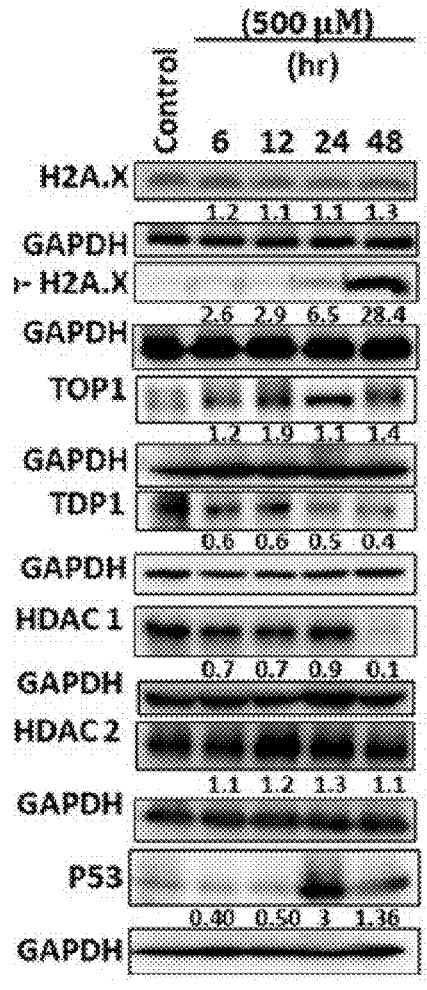
Figure 3B:
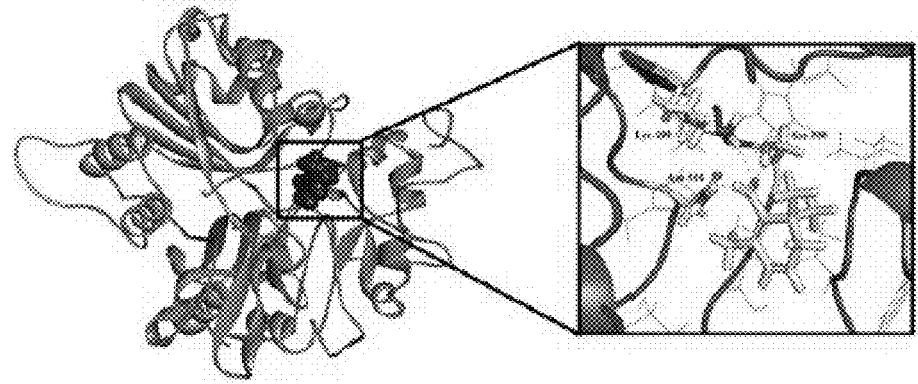
Figure 3C:
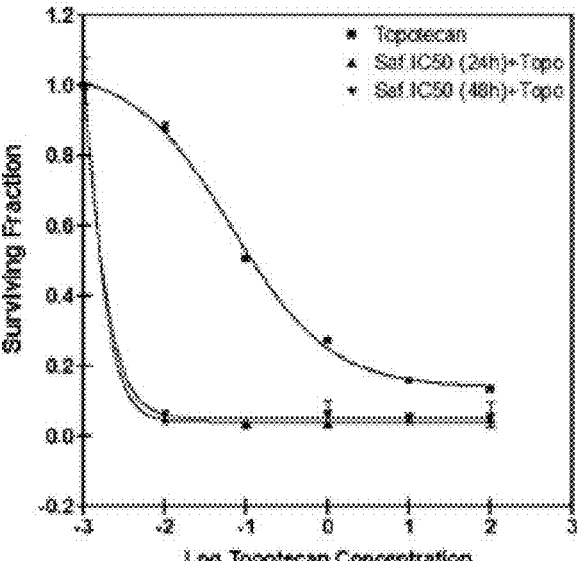

FIGS. 3A-3C establish that safranal exerts its cytotoxic effect by inducing DNA damage.

FIG. 3A provides a western blot analysis of key players in replication, proliferation, and DNA damage in HepG2 cells post treatment with safranal at a dose of 500 μM over a period of 48 hours. Each band intensity was quantified using ImageJ, normalized relative to their respective loading control bands. Values are expressed as ratio of untreated control. Western blot images of FIG. 3A have been cropped for clarity.

FIG. 3B illustrates docked poses of safranal within the human TDP1 active site.

FIG. 3C documents the enhancement of the cytotoxicity of topotecan by prior incubation with safranal. HepG2 cells were incubated with the topoisomerase 1 inhibitor topotecan alone or with IC50 safranal for 24 or 48 hours followed by topotecan; cell viability was measured by SRB assay.

FIGS. 4A-4E establish that safranal induces apoptosis of HepG2 cells.

Figure 4A:
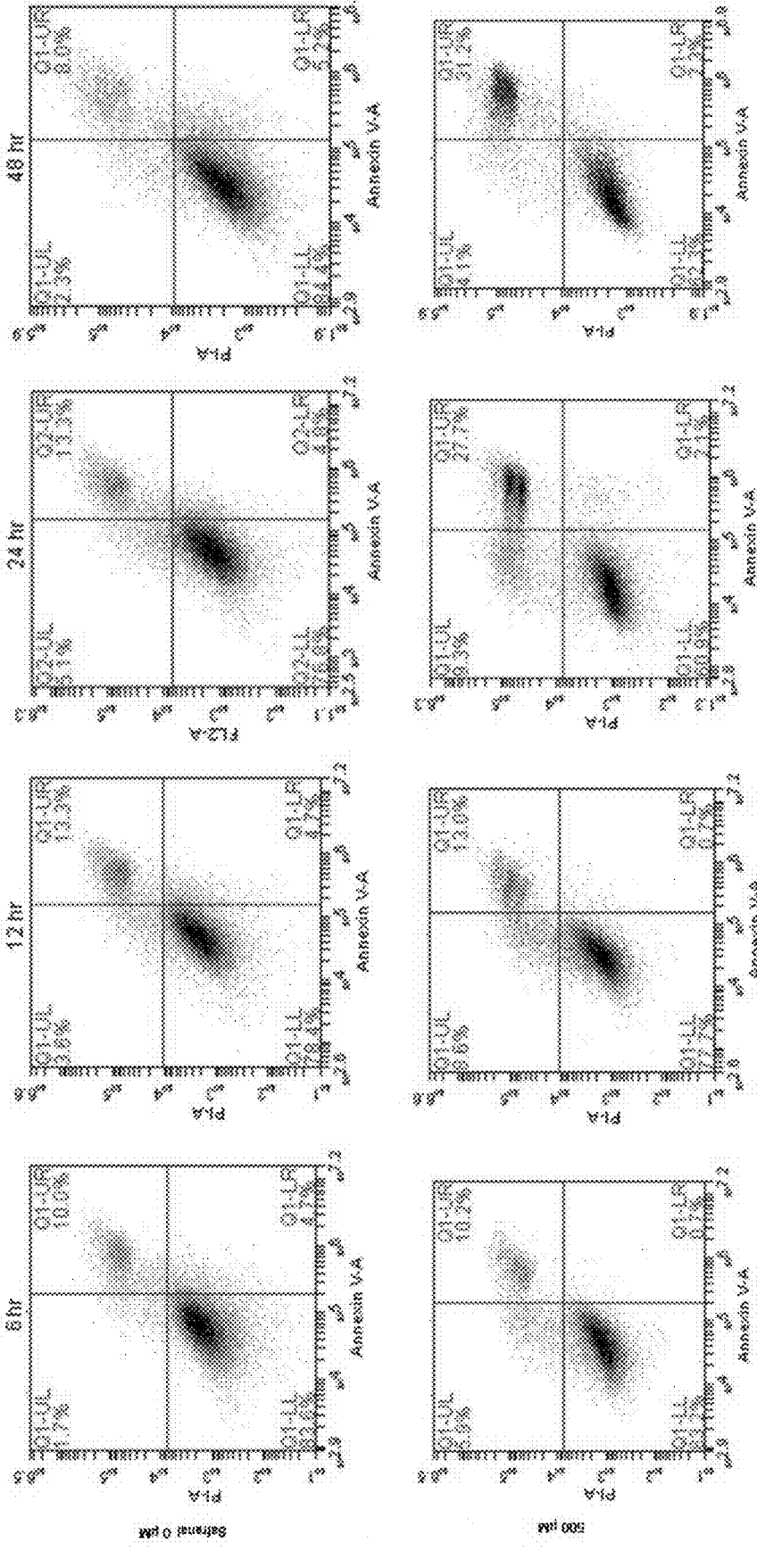

FIG. 4A provides an assessment of apoptosis by Annexin V on HepG2 cells treated with 500 μM of safranal over a period of 48 hours.

Figure 4B:
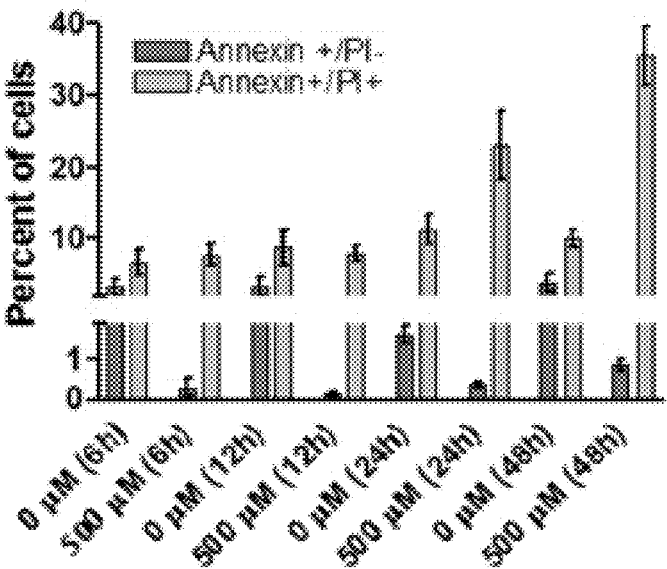

FIG. 4B reports a quantification of Annexin V analysis.

Figure 4C:
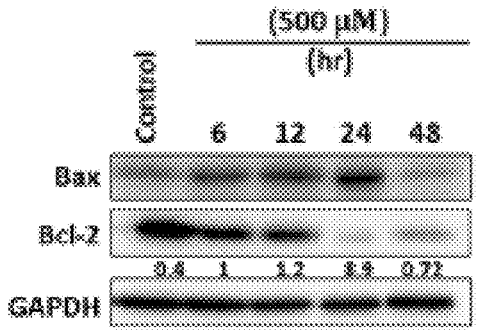

FIG. 4C reports a western blot analysis of apoptosis-related proteins in HepG2 cells treated with safranal in time-based experiments. Each band intensity was quantified using ImageJ, normalized relative to their respective loading control bands. Values are expressed as ratio of Bax to Bcl-2. The western blot image of FIG. 4C has been cropped for clarity.

Figure 4D:
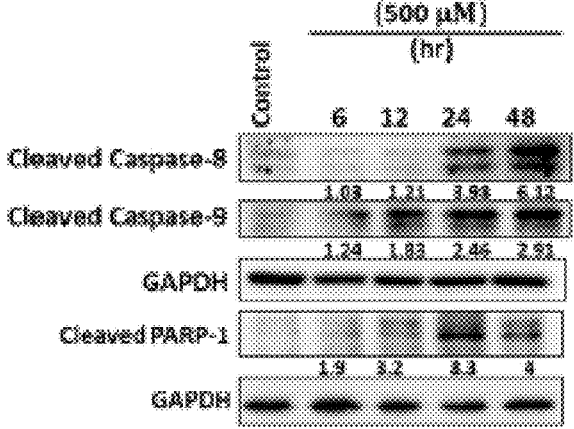

FIG. 4D provides a western blot analysis of caspases in HepG2 cells treated with safranal in time-based experiments. Each band intensity was quantified using ImageJ, normalized relative to their respective loading control bands. Values are expressed as ratio of untreated control. The western blot of FIG. 4D has been cropped for clarity.

Figure 4E:
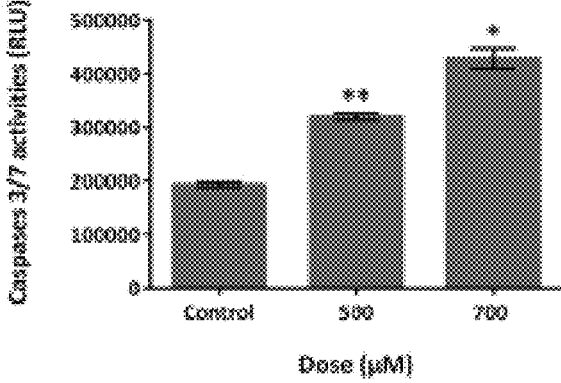

FIG. 4E reports caspase-3/7 activity in HepG2 cells treated with 500 and 700 μM of safranal for 24 hours. Student T-test was carried out (* p<0.05,p<0.001, *p<0.0001).

Figure 5:
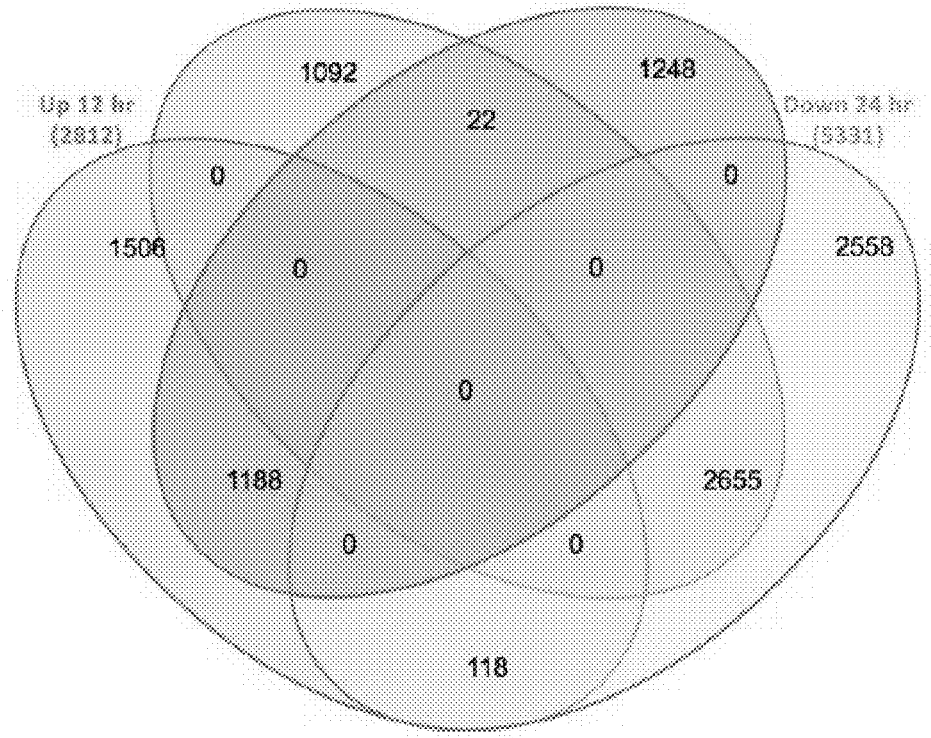

FIG. 5 provides a Venn diagram of differentially expressed genes at 12 and 24 hours after safranal treatment. The Venn diagram shows the distribution of up and down-regulated expressed genes between control and treatment after 12 hours and 24 hours (FDR≤0.05 and fold change of ≥0.58 log 2 fold (1.5 fold)).

Figure 6B:
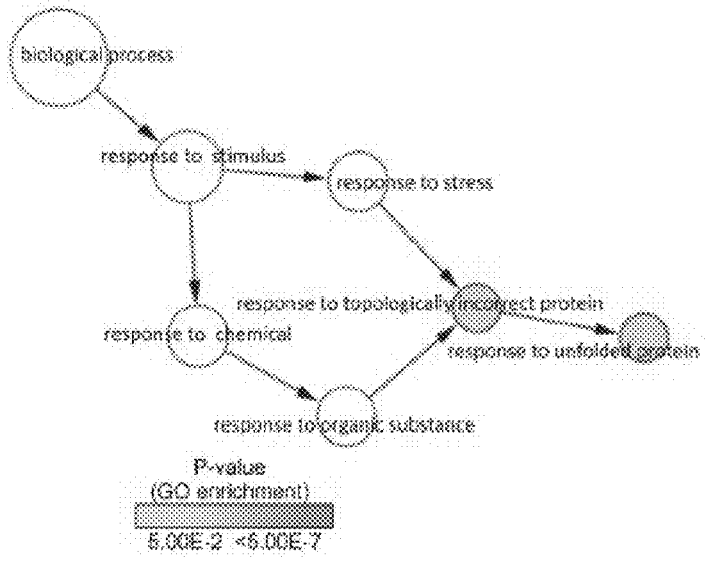
Figure 6C:
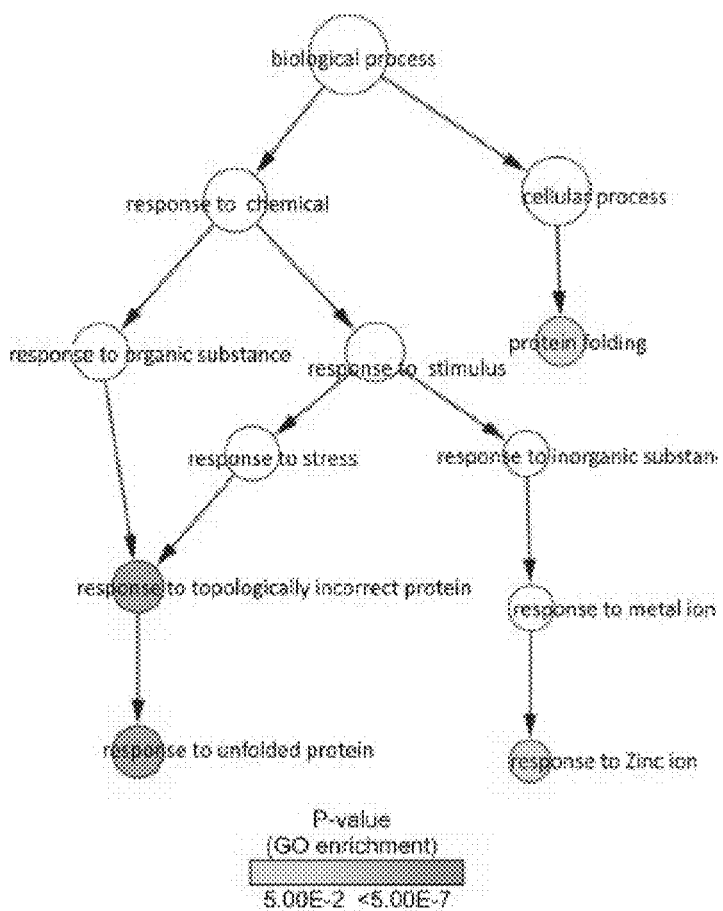

FIGS. 6A-6C illustrate the up- and down-regulation of genes following exposure to safranal.

FIG. 6A provides heatmaps of the top 50 differentially expressed genes. The heatmaps display the log 2 fold change of the top 50 genes (up and downregulated) at 12 and 24 hours after treatment.

FIG. 6B provides a GO term overrepresentation of the top up-regulated 100 genes at 12 hours.

FIG. 6C provides a GO term overrepresentation of the top up-regulated 100 genes at 24 hours. The size of each circle is correlated to the number of genes and the color of the nodes indicates different levels of significance for the enriched terms according to the provided key.

Figure 7:
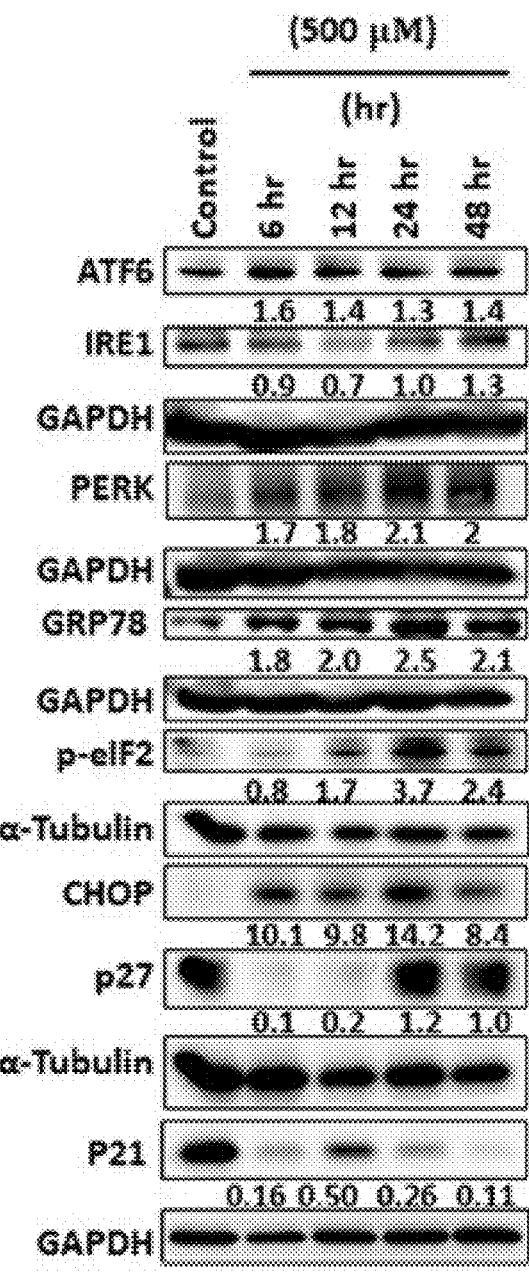

FIG. 7 proves that safranal induces ER stress by providing a western blot analysis of key players in UPR in HepG2 cells post treatment with safranal at a dose of 500 μM over a period of 48 hours. Each band intensity was quantified using ImageJ, normalized relative to their respective loading control bands. Values are expressed as ratio of untreated control. Western blot images have been cropped for clarity.

Figure 8:
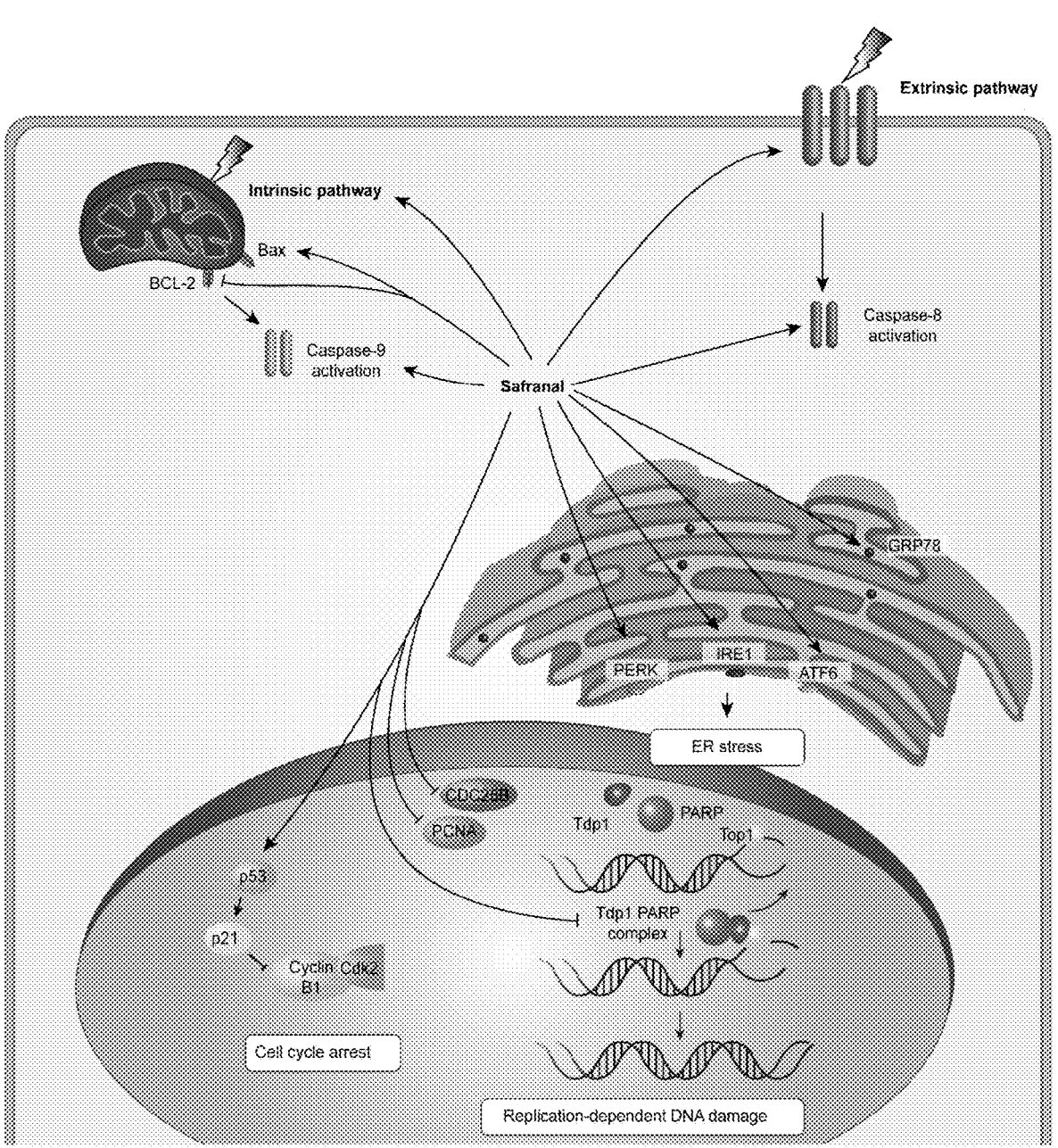

FIG. 8 is a schematic representation of safranal-mediated mechanisms against liver cancer cells.

Figure 9:
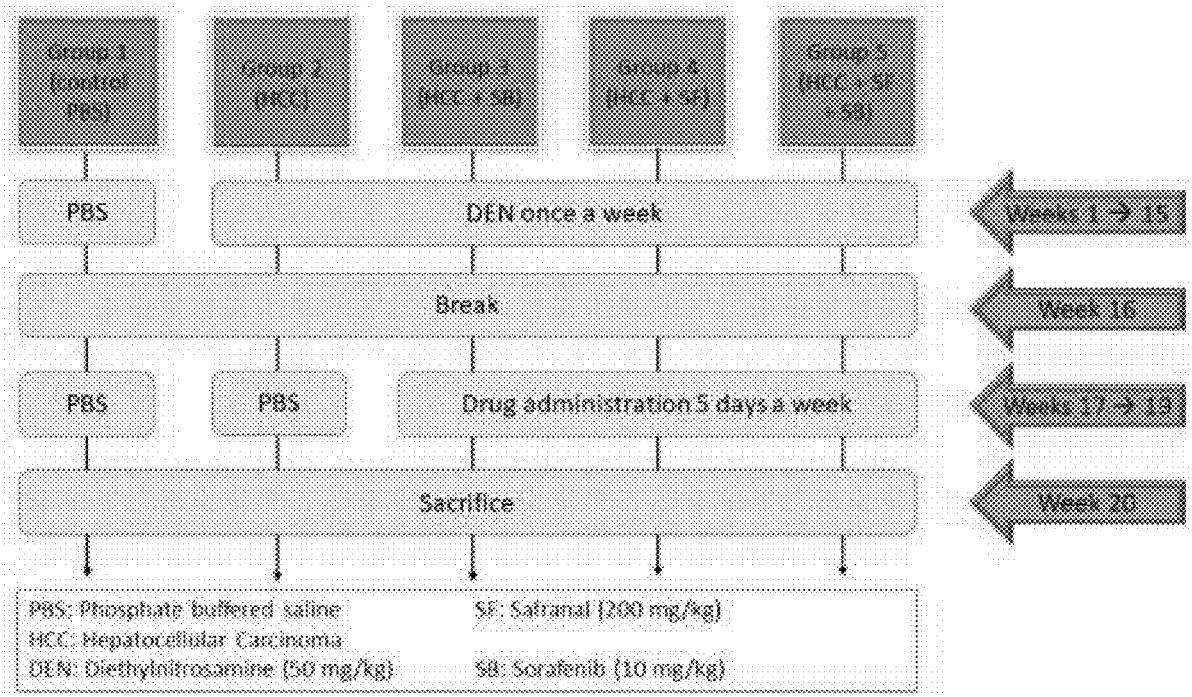

FIG. 9 provides the experimental design of an in vivo study conducted to establish a hepatocarcinogenesis model.

Figure 10:
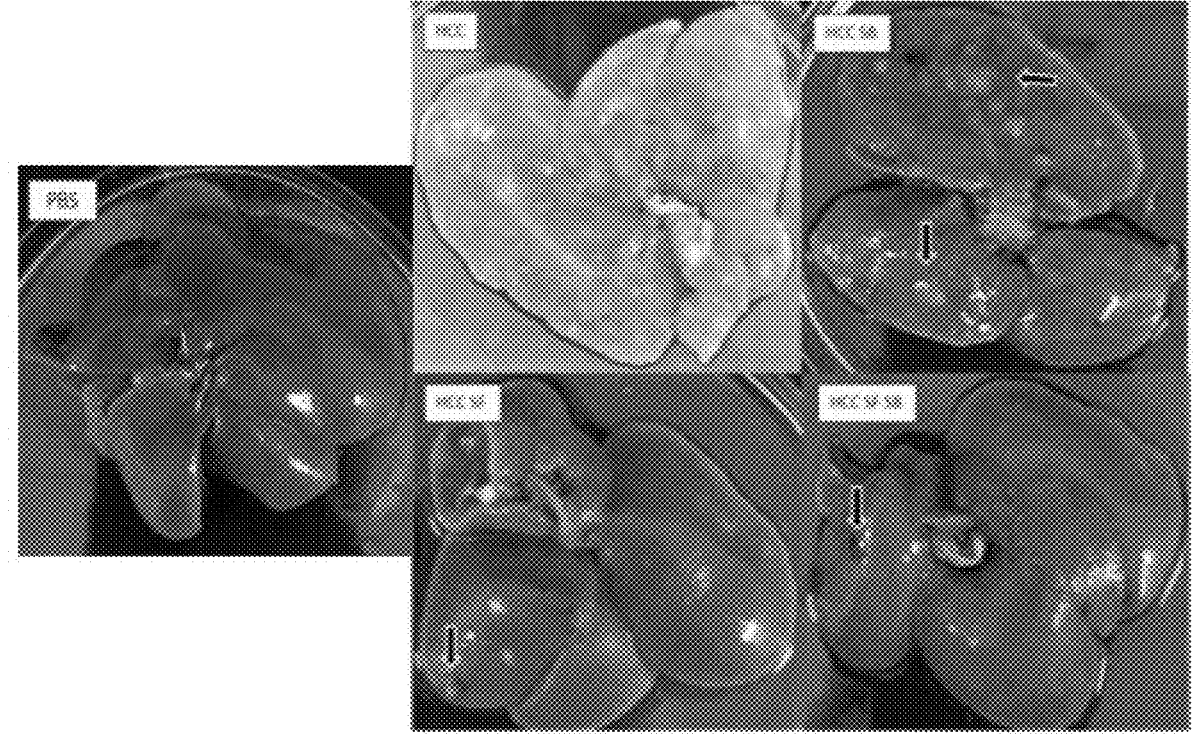

FIG. 10 provides representative images of rat livers demonstrating the anti-tumorigenic properties of safranal. Whole livers were excised from control rats (PBS), DEN-induced hepatic neoplasia in rats untreated (HCC group) or treated with sorafenib (HCC SB), safranal (HCC SF) individually or combined (HCC SF SB).

Figure 11:
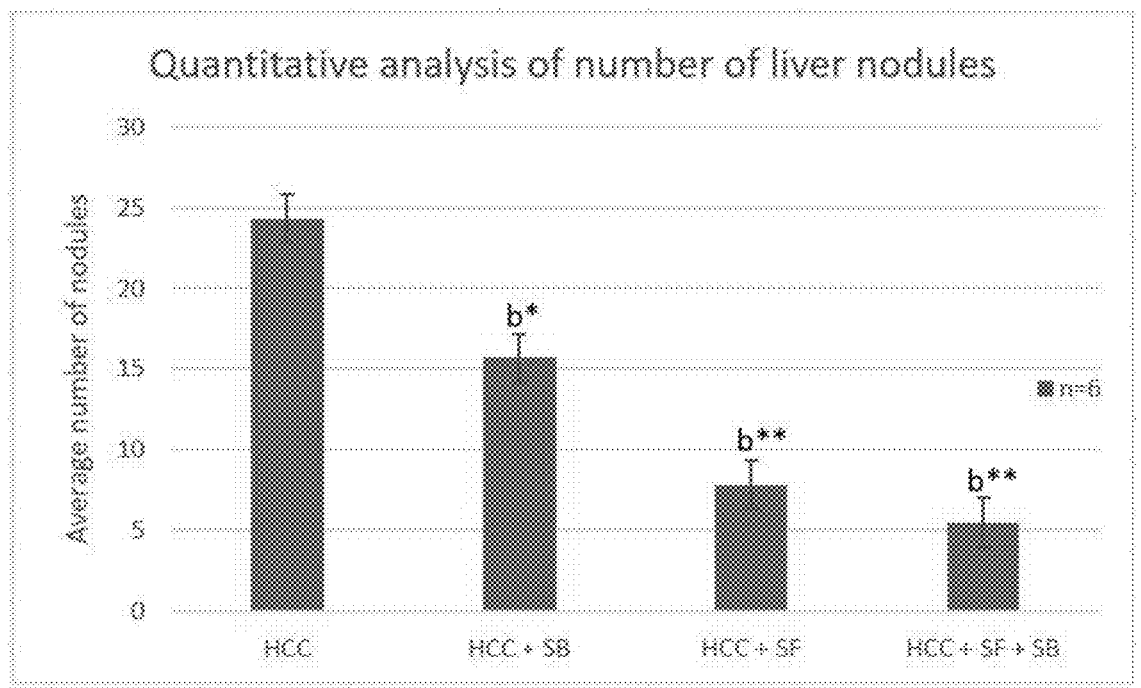

FIG. 11 provides a quantitative analysis of the number of liver nodules from DEN-induced hepatic neoplasia in rats untreated (HCC group) or treated with sorafenib (HCC+SB), safranal (HCC+SF) individually or combined (HCC+SF+SB).

Figure 12:
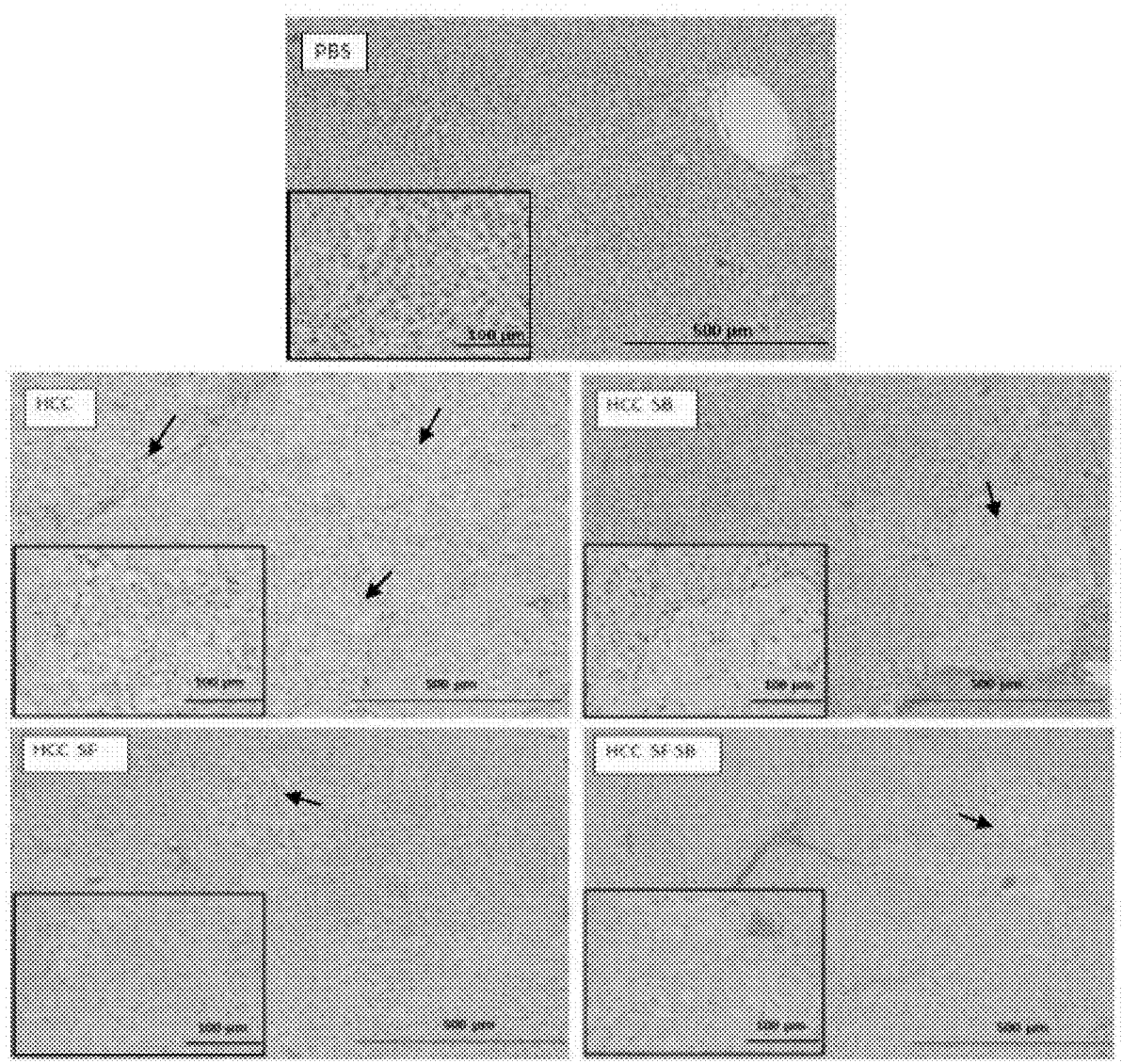

FIG. 12 provides representative images of hematoxylin and eosin-stained sections (arrows point to representative areas of AHF), n=6. The sections were of livers from control rats (PBS), DEN-induced hepatic neoplasia in rats untreated (HCC group) or treated with sorafenib (HCC SB), safranal (HCC SF) individually or combined (HCC SF SB).

Figure 13:
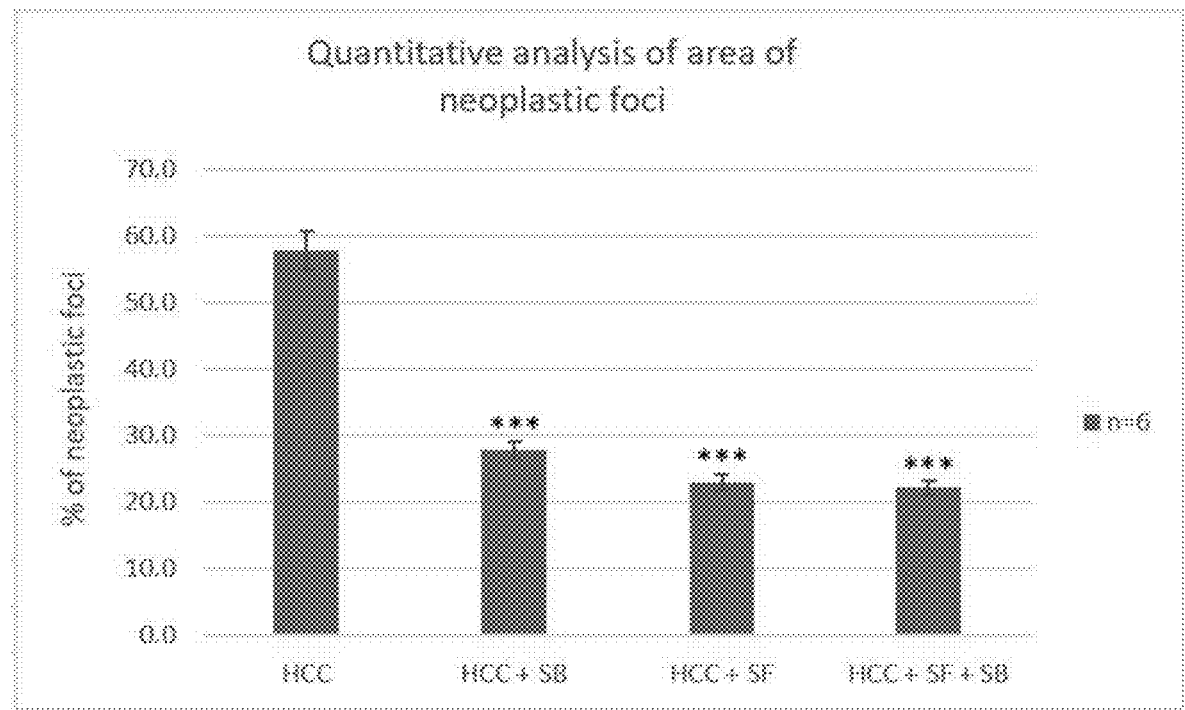

FIG. 13 provides a quantitative analysis of the area of neoplastic foci for histology from DEN-induced hepatic neoplasia in rats that were untreated (HCC group) or treated with sorafenib (HCC+SB), safranal (HCC+SF) individually or combined (HCC+SF+SB).

Figure 14:
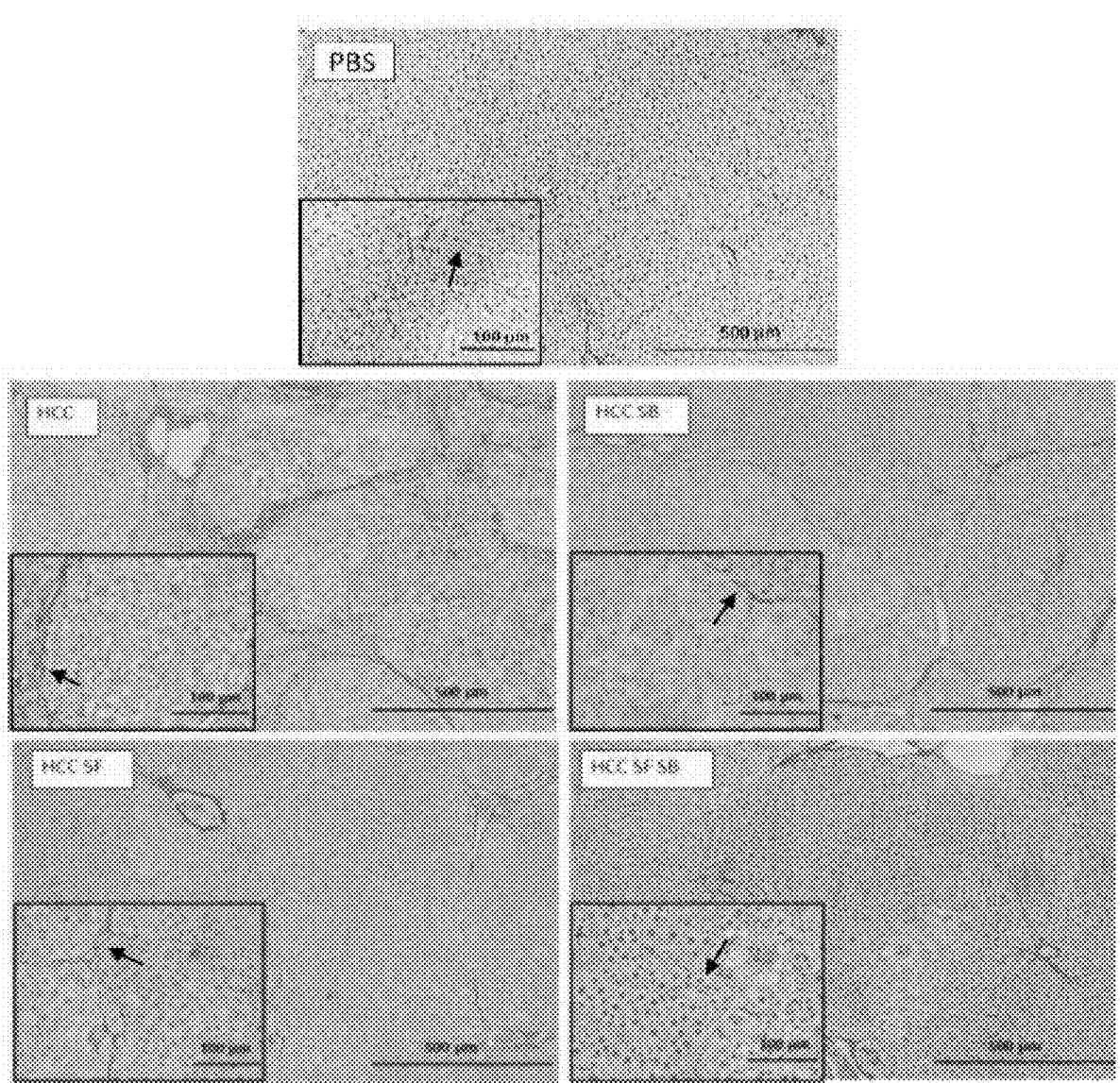

FIG. 14 provides representative images of reticulin-stained sections (arrows point to reticulin fibers). The sections were taken from control rats (PBS), DEN-induced hepatic neoplasia in rats untreated (HCC group) or treated with sorafenib (HCC SB), safranal HCC SF) individually or combined (HCC SF SB).

Figure 15A:
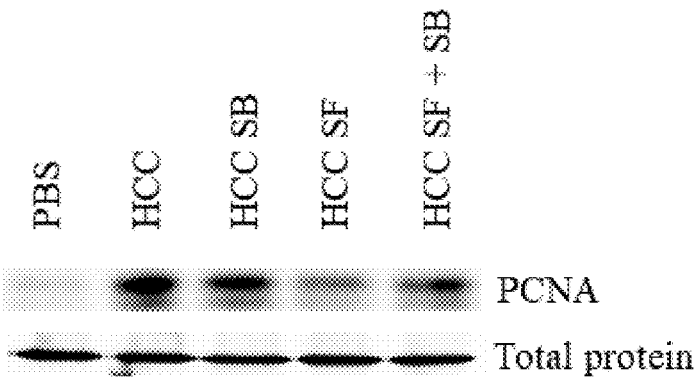
Figure 15B:
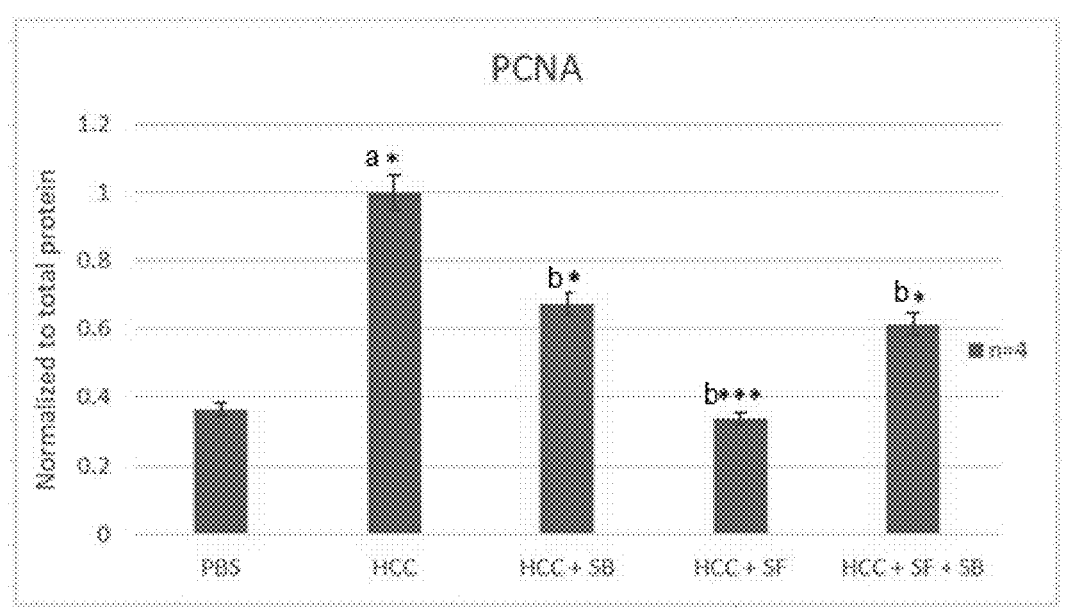

FIGS. 15A-15B demonstrate that safranal inhibits proliferation of induced hepatic neoplasia.

FIG. 15A is a western blot analysis of the proliferation-related protein (PCNA) on DEN-induced hepatic neoplasia in rats untreated (HCC group) or treated with sorafenib (HCC SB), safranal (HCC SF) individually or combined (HCC SF+SB).

FIG. 15B reports the quantification of each band intensity from FIG. 15A. Quantification was carried out using ImageJ, normalized in relative to the total protein from the liver.

Figure 16:
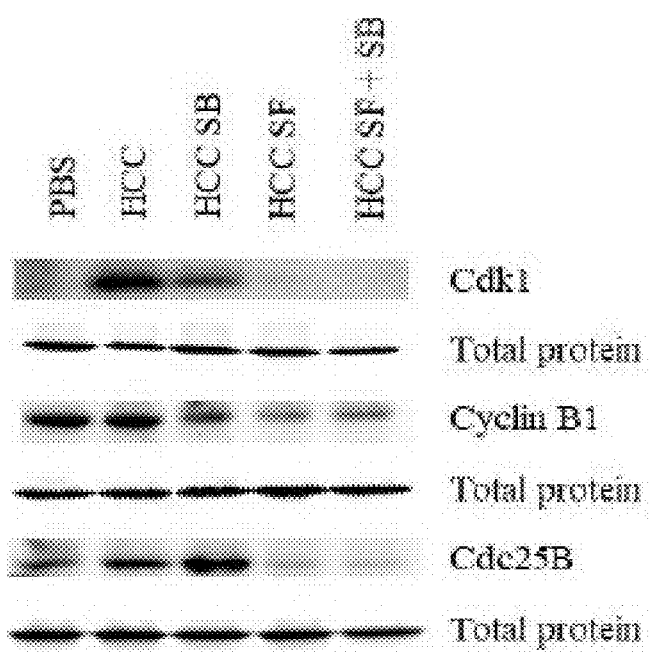

FIG. 16 is a western blot analysis of the cell cycle-related proteins (Cdk1, Cyclin B1, Cdc25B) on DEN-induced hepatic neoplasia in rats untreated (HCC group) or treated with sorafenib (HCC SB), safranal (HCC SF) individually or combined (HCC SF+SB).

Figure 17:
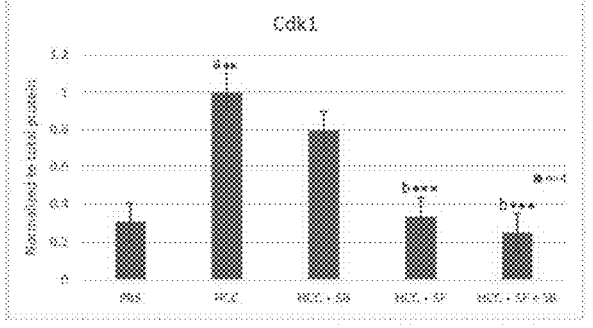
Figure 17:
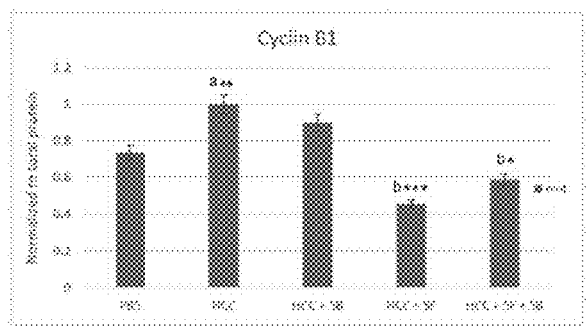

FIG. 17 reports the quantification of proteins of G2/M cell cycle arrest of induced hepatic neoplasia. Each band intensity from FIG. 16 was quantified using ImageJ, normalized in relative to the total protein from the liver. Results are expressed as mean±S.D for n=4 animals in each group. Statistical significance was determined using Microsoft Excel Data Analysis Tool Pack, t-test: two-sample assuming equal variances.

Figure 18:
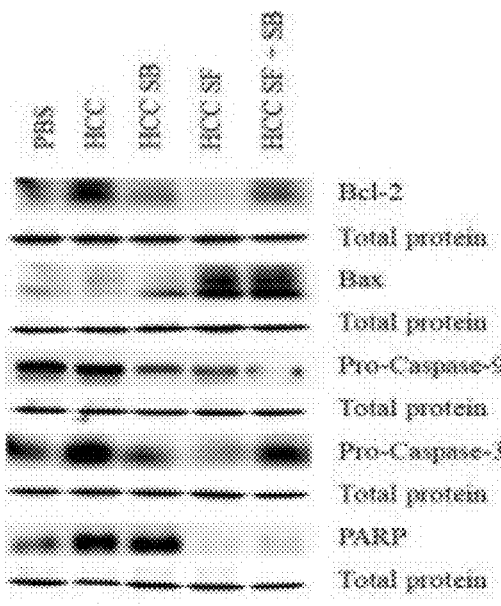

FIG. 18 is a western blot analysis establishing that safranal induces intrinsic apoptosis of induced hepatic neoplasia. The western blot analyzes the intrinsic apoptosis-related proteins (Bcl-2, Bax, Pro-Caspase-9, Pro-Caspase-3, PARP) on DEN-induced hepatic neoplasia in rats untreated (HCC group) or treated with sorafenib (HCC SB), safranal (HCC SF) individually or combined (HCC SF+SB).

Figure 19:
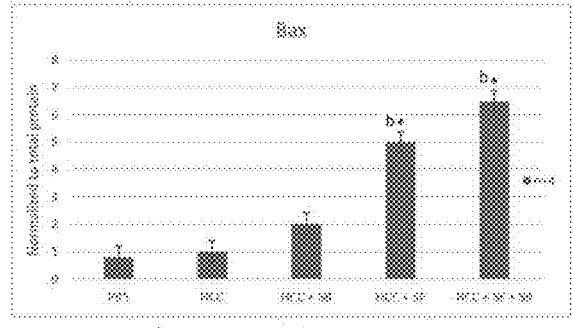
Figure 19:
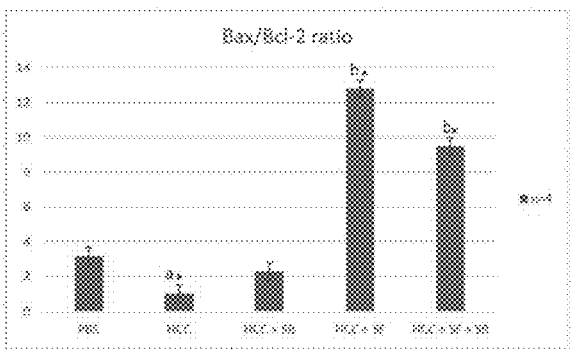

FIG. 19 provides the results of a quantification of Bax, Bcl-2, and the Bax/Bcl ratio from the bands of the western blot of FIG. 18. Each band intensity was quantified using ImageJ, normalized in relative to the total protein from the liver. Results are expressed as mean±S.D for n=4 animals in each group. Statistical significance was determined using Microsoft Excel Data Analysis Tool Pack, t-test: two-sample assuming equal variances.

Figure 20:
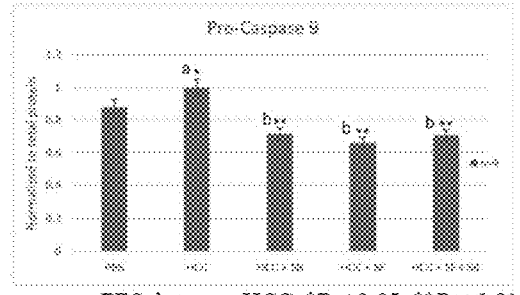
Figure 20:
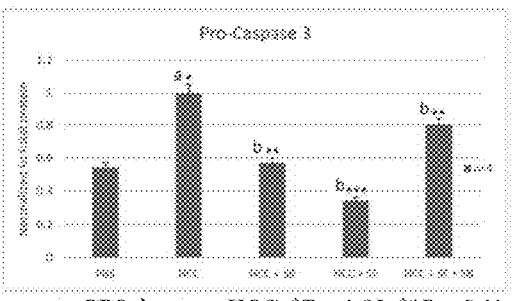
Figure 20:
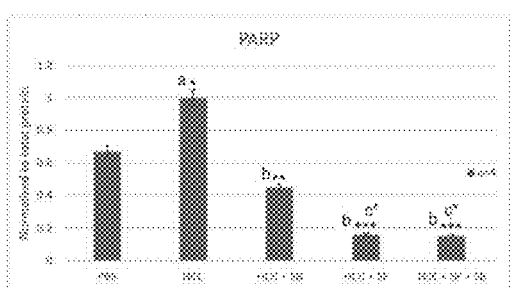

FIG. 20 provides the results of a quantification of Pro-Caspase-9, Pro-Caspase-3, and PARP from the bands of the western blot of FIG. 18. Each band intensity was quantified using ImageJ, normalized in relative to the total protein from the liver. Results are expressed as mean±S.D for n=4 animals in each group. Statistical significance was determined using Microsoft Excel Data Analysis Tool Pack, t-test: two-sample assuming equal variances.

Figure 21:
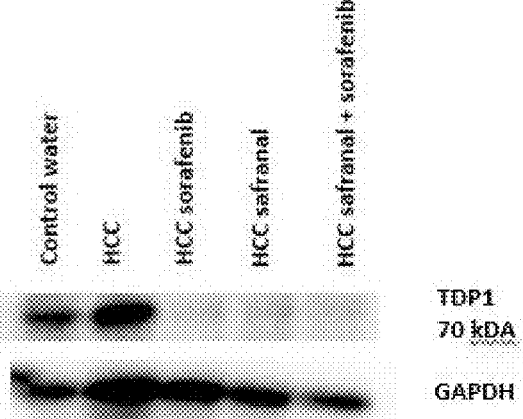

FIG. 21 is a western blot analysis proving that safranal induces lower levels of tyrosyl-DNA-phosphodiesterase (TDP1) on DEN-induced HCC in rats untreated (HCC group) or treated with sorafenib (HCC SB), safranal (HCC SF) individually or combined (HCC SF+SB).

FIG. 22 is a table reporting human equivalent dose (HED) dosage factors based on body surface area of other species according to data obtained from Food and Drug Administration draft guidelines.

DETAILED DESCRIPTION

The present invention is based on the finding that safranal exerts an anticancer effect on HepG2 cells and on HCC in laboratory rats. This therapeutic effect can put to use in the treatment of liver cancer. Therefore, provided herein is a method of treating, suppressing, or reducing the severity of a liver cancer in a subject by administering to the subject a therapeutically effective amount of a composition including safranal or its pharmaceutically acceptable pro-drug (for example a salt, hydrate, hemiacetal, acetal, thioacetal, silylether, tautomer, or isomer) either alone or combined with a pharmaceutically acceptable carrier.

Without being bound to any theory, it is believed that safranal exerts its anticancer effect in HepG2 cells by interfering with DNA replication and inhibiting DNA repair, resulting in increased DNA damage. Inhibited protein expression of main contributors of DNA DSB repair mechanism such as TDP1, HDAC1 and HDAC2 clearly support that notion, which is particularly evident in safranal inhibition of TDP1, a strong contributor to the DNA DSB repair mechanism, as revealed by molecular docking, immunoblotting, and SRB assay.

Importantly, it has also been found that treatment with safranal induces an increased sensitivity in cancerous cells to Type I topoisomerase (TOP1) inhibitors such as topotecan. Hence, also provided herein is a method of treating, suppressing, or reducing the severity of a liver cancer in a subject including administering to the subject a first amount of safranal (or its pharmaceutically acceptable salt, hydrate, hemiacetal, acetal, thioacetal, silylether, tautomer, or isomer) and administering to the subject a second amount of a TOP1 inhibitor.

Again without being bound to any particular theory, the above sensitization may indicate that treatment with safranal inhibits TDP1 that is needed for the repair of topotecan-induced TOP1-DNA complexes. Also, HDAC1 and HDAC2 participate in the DNA damage response, where they facilitate repair of DSB [37]. Indeed, cells that were HDAC1 and HDAC2 depleted have been shown to be hypersensitive to DNA-damaging agents, suggesting a defective DSB repair.

DNA damage arising from conventional cancer therapy (e.g. chemotherapy and radiation) is recognized by DNA repair machinery of cancer cells, which leads to drug resistance [12]. By inhibiting TDP1 and hindering DNA repair, more effective cancer therapeutics can be developed [13]. However, traditional TDP1 inhibitors are scarce and only few are effective at inhibiting TDP1 expression at micromolar concentrations [14]. In contrast, 500 µM of safranal was found to inhibit TDP1 expression at 24 hours and nearly abolished it at 48 hours, despite the increase in the expression of TOP1. Hence, the inhibition of TDP1 by safranal may be used to increase the cytotoxic effect of TOP1 inhibitors on cancer cells.

In addition, provided herein are therapeutic combinations of drugs including a first amount of safranal (or its pharmaceutically acceptable pro-drug) and a second amount of a TOP1 inhibitor. Essentially, the combination of safranal and the TOP1 inhibitor represents a therapeutic combination that may be more efficacious than either agent alone or the simple sum of the two agents. In addition, different doses of the combination may lead to additional gains in treatment of the liver cancer than either safranal or the TOP1 inhibitor alone.

Safranal Compositions

In a first aspect, the present application provides therapeutic compositions and methods to treat, suppress, or reduce the severity of liver cancer in a subject by administering a therapeutically effective amount of a composition including safranal or its pharmaceutically acceptable pro-drug, either alone or formulated together with one or more pharmaceutically acceptable carrier(s), diluent(s), or excipient(s). The carrier(s), diluent(s) or excipient(s) must be acceptable in the sense of being compatible with the other ingredients of the formulation, capable of pharmaceutical formulation, and not deleterious to the recipient thereof.

As illustrated above, safranal includes an α-β unsaturated aldehyde group and is therefore capable of forming hemiacetals, acetals, thioketals, silyl ethers, and other derivatives resulting from nucleophilic addition reactions to the β-carbon of the unsaturation. In instances where the safranal derivatives are pharmaceutically acceptable and easily cleavable under physiological conditions, one or more derivative may be administered to the patient as a pro-drug of safranal itself. The term "pharmaceutically acceptable safranal derivative", in this respect, refers to the pharmaceutically acceptable and easily cleavable groups of safranal, including hemiacetals, acetals, thioketals, silyl ethers, and nucleophilic addition products. These pro-drugs can be prepared in situ in the administration vehicle or in the dosage form manufacturing process, or by separately reacting safranal with a suitable reactant, and isolating the derivative thus formed during subsequent purification. Other derivatives that may serve as pro-drugs include pharmaceutically acceptable salts and hydrates. Therapeutically effective tautomers and isomers of safranal are also contemplated. Unless otherwise specified, the terms "composition including safranal" and "formulation of safranal" as used herein are intended to cover compositions and formulations including safranal itself, its pro-drugs such as hemiacetals and acetals, pharmaceutically acceptable tautomers and isomers, and pharmaceutically acceptable salts thereof.

The composition may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of safranal include those suitable for oral, nasal, topical (including buccal and sublingual), rectal, vaginal and/or parenteral administration. The formulations may conveniently be presented in unit dosage form and may be prepared by any methods well known in the art of pharmacy. The amount of safranal or its pharmaceutically acceptable pro-drugs which can be combined with a carrier material to produce a single dosage form will vary depending upon the host being treated, the particular mode of administration. The amount of an active ingredient which can be combined with a carrier material to produce a single dosage form will usually be that amount of the compound which produces a therapeutic effect. Usually, out of one hundred percent, this amount will range from about 1 wt % to about 99 wt % of active ingredient, preferably from about 5 wt % to about 70 wt %, most preferably from about 10 wt % to about 30 wt %.

In certain embodiments, a formulation of safranal includes an excipient selected from the group consisting of cyclodextrins, liposomes, micelle forming agents, e.g., bile acids, and polymeric carriers, e.g., polyesters and polyanhydrides; and an active ingredient that may be safranal and/or one of its pharmaceutically acceptable derivatives. In certain embodiments, an aforementioned formulation renders orally bioavailable safranal or its derivative.

Methods of preparing these formulations or compositions include the step of bringing into association safranal with the carrier and, optionally, one or more accessory ingredients. Usually, the formulations are prepared by uniformly and intimately bringing into association a compound of the present invention with liquid carriers, or finely divided solid carriers, or both, and then, if necessary, shaping the product.

Liquid dosage forms for oral administration of safranal include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents. Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A formulation of safranal may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also include buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

The tablets, and other solid dosage forms of the pharmaceutical of safranal or its pro-drugs, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Formulations of the pharmaceutical compositions of safranal for rectal or vaginal administration may be presented as a suppository, which may be prepared by mixing safranal with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Dosage forms for the topical or transdermal administration of safranal include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required. The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compounds, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of safranal or its pro-drugs to the body. Such dosage forms can be made by dissolving or dispersing a compound in the proper medium. Absorption enhancers can also be used to increase the flux of the compound across the skin. The rate of such flux can be controlled by either providing a rate controlling membrane or dispersing the compound in a polymer matrix or gel.

Pharmaceutical compositions suitable for parenteral administration include one or more of safranal or its pro-drugs in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When safranal is administered as a pharmaceutical composition, to humans and animals, it can be given per se or as a pharmaceutical composition containing, for example, 0.1 to 99.5% (more preferably, 0.5 to 90%) of active ingredient in combination with a pharmaceutically acceptable carrier.

The preparations may be given orally, parenterally, topically, or rectally. They are of course given in forms suitable for each administration route. For example, they are administered in tablets or capsule form, by injection, inhalation, eye lotion, ointment, or suppository; administration by injection, infusion or inhalation; topical by lotion or ointment; and rectal by suppositories. Oral administrations are preferred.

Safranal may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, safranal or its pro-drugs may be formulated into pharmaceutically-acceptable dosage forms by conventional methods known to those of skill in the art. Safranal may be formulated for administration in any convenient way for use in human or veterinary medicine, by analogy with other pharmaceuticals.

In certain embodiments, the above-described pharmaceutical compositions include safranal, a second therapeutic agent, and optionally a pharmaceutically acceptable carrier. Alternatively, The terms "chemotherapeutic agent" or "therapeutic agent" include, without limitation, platinum-based agents, such as carboplatin and cisplatin; nitrogen mustard alkylating agents; nitrosourea alkylating agents, such as carmustine (BCNU) and other alkylating agents; antimetabolites, such as methotrexate; purine analog antimetabolites; pyrimidine analog antimetabolites, such as fluorouracil (5-FU) and gemcitabine; hormonal antineoplastics, such as goserelin, leuprolide, and tamoxifen; natural antineoplastics, such as taxanes (e.g., docetaxel and paclitaxel), aldesleukin, interleukin-2, etoposide (VP-16), interferon alfa, and tretinoin (ATRA); antibiotic natural antineoplastics, such as bleomycin, dactinomycin, daunorubicin, doxorubicin, and mitomycin; and vinca alkaloid natural antineoplastics, such as vinblastine and vincristine.

As reported above, it has been found that treatment with safranal induces an increased sensitivity in cancerous cells to Type I topoisomerase (TOP1) inhibitors such as topotecan. Hence, in some embodiments, the second therapeutic agent is a TOP1 inhibitor, for example irinotecan, topotecan, camptothecin, or lamellarin D, and provided herein are combinations of drugs including safranal and a TOP1 inhibitor. It will be recognized by one of skill in the art that the respective amounts of safranal and TOP1 inhibitor in the pharmaceutical composition of this aspect of the invention may vary quite widely depending upon numerous factors, such as the choice of TOP1 inhibitor, the desired dosage and the pharmaceutically acceptable carrier being employed. For administration, the content of the TOP1 inhibitor will usually be 0.1:1 to 10:1 by weight, with respect to the content of the safranal present in the composition. Preferably, the relative amounts of safranal and TOP1 inhibitor will be such that therapeutic synergism, that is, an effect greater than can be achieved with either agent used individually at its maximally treated dose, is achieved.

Methods of Liver Cancer Treatment

The above safranal compositions may be used in novel therapeutic methods of treating liver cancer. The methods include administering to the subject an effective amount of a subject pharmaceutical safranal composition. In some embodiments, the type of liver cancer is a hepatocellular carcinoma (HCC), fibrolamellar HCC, cholangiocarcinoma, angiosarcoma, or a metastatic liver cancer.

Safranal may be administered by any appropriate route. It will be appreciated that the preferred route may vary with, for example, the condition of the recipient of the safranal and the cancer to be treated. In certain embodiments, the method includes parenterally administering an effective amount of a subject pharmaceutical composition to a subject. In an embodiment, the method includes intraarterial administration of a subject composition to a subject. In other embodiments, the method comprises administering an effective amount of a subject composition directly to the arterial blood supply of a liver cancer in a subject. In an embodiment, the methods comprises administering an effective amount of a subject composition directly to the arterial blood supply of the cancer using a catheter. In another embodiment, the method comprises chemoembolization. For example a chemoembolization method may comprise blocking a vessel feeding the cancer with a composition comprised of a resin-like material mixed with an oil base and one or more chemotherapeutic agents. In still other embodiments, the method comprises systemic administration of a subject composition to a subject.

Also provided are methods of treating liver cancer that include administering safranal in conjunction with a second therapeutic agent to a subject. Conjunctive therapy includes sequential, simultaneous and separate, or co-administration of the safranal and the second therapeutic agent in a way that the therapeutical effect of the safranal is not entirely disappeared when the second therapeutic agent is administered. In certain embodiments, safranal and the second chemotherapeutic agent may be compounded together in the same unitary pharmaceutical composition including both compounds. Alternatively, the combination of safranal and second therapeutic agent may be administered separately in separate pharmaceutical compositions, each including one of the safranal and chemotherapeutic agent in a sequential manner wherein, for example, safranal or the second therapeutic agent is administered first and the other second.

Combinations of Safranal and TOP1 Inhibitors

As reported above, it has been found that treatment with safranal induces an increased sensitivity in cancerous cells to Type I topoisomerase (TOP1) inhibitors such as topotecan. Hence, in some embodiments, the second therapeutic agent is a TOP1 inhibitor, for example irinotecan, topotecan, camptothecin, and lamellarin D, for the purpose of treating cancer. In certain embodiments of the combination, safranal and the TOP1 inhibitor may be compounded together in the same unitary pharmaceutical composition including both compounds. Alternatively, the combination of safranal and TOP1 inhibitor may be administered separately in separate pharmaceutical compositions, each including one of the safranal and TOP1 inhibitor, in a sequential manner wherein, for example, safranal or topotecan is administered first and the other second. Such sequential administration may be close in time (e.g. simultaneously) or remote in time. Furthermore, it does not matter if the compounds are administered in the same dosage form, e.g. one compound may be administered topically and the other compound may be administered orally. In an embodiment, both compounds are administered orally. Thus, in an embodiment, one or more doses of safranal are administered simultaneously or separately with one or more doses of TOP1 inhibitor.

It will be recognized by one of skill in the art that the respective amounts of safranal and TOP1 inhibitor may vary quite widely depending upon numerous factors, such as the choice of TOP1 inhibitor, the desired dosage and the pharmaceutically acceptable carrier being employed. For administration, the amount of safranal will usually be 0.1:1 to 10:1 by weight, with respect to the amount of the TOP1 inhibitor. Preferably, the relative amounts of safranal and TOP1 inhibitor will be such that therapeutic synergism, that is, an effect greater than can be achieved with either agent used individually at its maximally treated dose, is achieved.

Administration of Therapeutic Compositions

In representative embodiments, the methods of treating a cancer include administering an effective amount of a subject composition directly to the blood vessels in the liver. For example, blood vessels such as the hepatic artery may be infused, injected, chemoembolized, or catheterized to administer the subject compositions to a liver cancer. In other embodiments, the methods include administering an effective amount of a subject composition directly to the blood vessels in a cancer in the liver. Such methods are well-known and used in the art.

Usually, chemoembolization or direct intraarterial or intravenous injection therapy utilizing pharmaceutical compositions is typically performed in the following manner, regardless of the site. Briefly, angiography (a road map of the blood vessels), or more specifically in certain embodiments, arteriography, of the area to be embolized may be first performed by injecting a contrast agent through a catheter inserted into an artery or vein (depending on the site to be embolized or injected) as an X-ray, computed tomography (CT), or magnetic resonance image (MRI) is taken. The catheter may be inserted either percutaneously or by surgery. The blood vessel may be then embolized by refluxing pharmaceutical compositions including safranal through the catheter, until flow is observed to cease. Occlusion may be confirmed by repeating the angiogram. In embodiments where direct injection is used, the blood vessel is then infused with a pharmaceutical composition of safranal in the desired dose.

Embolization therapy usually results in the distribution of pharmaceutical compositions throughout the interstices of the tumor or vascular mass to be treated. The physical bulk of the embolic particles clogging the arterial lumen results in the occlusion of the blood supply. In addition to this effect, the presence of an anti-angiogenic factor(s) prevents the formation of new blood vessels to supply the tumor or vascular mass, enhancing the devitalizing effect of cutting off the blood supply. Direct intraarterial or intravenous usually results in distribution of compositions containing safranal throughout the interstices of the tumor or vascular mass to be treated as well. However, the blood supply is not usually expected to become occluded with this method.

In some embodiments, primary and secondary tumors of the liver may be treated utilizing embolization or direct intraarterial or intravenous injection therapy. Briefly, a catheter is inserted via the femoral or brachial artery and advanced into the hepatic artery by steering it through the arterial system under fluoroscopic guidance. The catheter is advanced into the hepatic arterial tree as far as necessary to allow complete blockage of the blood vessels supplying the tumor(s), while sparing as many of the arterial branches supplying normal structures as possible. Ideally, this will be a segmental branch of the hepatic artery, but it could be that the entire hepatic artery distal to the origin of the gastroduodenal artery, or even multiple separate arteries, will need to be blocked depending on the extent of tumor and its individual blood supply. Once the desired catheter position is achieved, the artery is embolized by injecting compositions (as described above) through the arterial catheter until flow in the artery to be blocked ceases, preferably even after observation for 5 minutes. Occlusion of the artery may be confirmed by injecting a contrast agent through the catheter and demonstrating by an imaging technique that the vessel which previously filled with contrast no longer does so. In embodiments where direct injection is used, the artery is infused by injecting compositions (as described above) through the arterial catheter in a desired dose. The same procedure may be repeated with each feeding artery to be occluded.

For use in embolization therapy, compositions of safranal are preferably non-toxic, thrombogenic, easy to inject down vascular catheters, rapid and permanent in effect, sterile, and readily available in different shapes or sizes at the time of the procedure. In some embodiments, the compositions result in the slow (ideally, over a period of 6 hours to a day) release of a second therapeutic agent following delivery of the safranal. In some embodiments, the subject pharmaceutical compositions will incorporate safranal and an optional second therapeutic agent to be delivered in an amount sufficient to deliver to a patient a therapeutically effective amount of safranal as part of a prophylactic or therapeutic treatment.

The desired concentration of safranal in the composition will depend on absorption, inactivation, and excretion rates of the safranal as well as the delivery rate of the compound. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

Alternatively, the dosage of safranal may be determined by reference to its concentration in the plasma. For example, the maximum plasma concentration ($C_{max}$) and the area under the plasma concentration-time curve from time 0 to infinity (AUC (0-4)) may be used. Dosages for the present invention include those that produce the above values for $C_{max}$ and AUC (0-4) and other dosages resulting in larger or smaller values for those parameters.

Actual dosage levels of the active ingredients in the pharmaceutical compositions of this aspect of the invention may be varied so as to obtain an amount of safranal which is effective to achieve the desired therapeutic response for a particular patient, composition, and mode of administration, without being toxic to the patient.

The selected dosage level will depend upon a variety of factors including the activity of the safranal (or its pro-drugs such as pharmaceutically acceptable hemiacetals and acetals, pharmaceutically acceptable tautomers and isomers, and pharmaceutically acceptable salts thereof), the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

Usually, a suitable daily dose of safranal that is contained in the therapeutic amount of the composition will be that amount of safranal which is the lowest dose effective to produce a therapeutic effect. Such an effective dose will usually depend upon the factors described above. If desired, the effective daily dose of safranal may be administered as two, three, four, five, six or more sub-doses administered separately at appropriate intervals throughout the day, optionally, in unit dosage forms. The precise time of administration and amount of any particular compound that will yield the most effective treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

Exemplary doses of safranal fall in the range from about 0.001, 0.01, 0.1, 0.5, 1, 10, 15, 20, 25, 50, 100, 200, 300, 400, 500, 600, or 750 to about 1000 mg/day per kg body weight of the subject. In certain embodiments, the dose of safranal will typically be in the range of about 100 mg/day to about 1000 mg/day per kg body weight of the subject, specifically in the range of about 200 mg/day to about 750 mg/day per kg, and more specifically in the range of about 250 mg/day to about 500 mg/day per kg. In an embodiment, the dose is in the range of about 50 mg/day to about 250 mg/day per kg. In a further embodiment, the dose in the range of about 100 mg/day to about 200 mg/day per kg. In an embodiment, the dose is in the range of about 15 mg/day to 60 mg/day per kg. In a further embodiment, the dose is in the range of about 20 mg/day to 50 mg/day per kg. In an additional embodiment, the dose is in the range of about 25 mg/day to 45 mg/day per kg.

The combined use of safranal and other chemotherapeutic agents, such as TOP1 inhibitors, may reduce the required dosage for any individual component because the onset and duration of effect of the different components may be complimentary. In such combination therapies, the different active agents may be delivered together or separately, and simultaneously or at different times within the day.

The data obtained from the cell culture assays and animal studies may be used in formulating a range of dosage for use in humans. For example, effective dosages achieved in one animal species may be extrapolated for use in another animal, including humans, as illustrated in the conversion table of FIG. 22 where human equivalent dose (HED) dosage factors based on body surface area of other species are reported. (Nair and Jacob, 2016). The dosage of any supplement, or alternatively of any components therein, lies preferably within a range of circulating concentrations that include the $ED_{50}$ with little or no toxicity. The dosage may vary within this range depending upon the dosage form employed and the route of administration utilized. For safranal or combinations of safranal and other chemotherapeutic agents, the therapeutically effective dose may be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information may be used to more accurately determine useful doses in humans. Levels in plasma may be measured, for example, by high performance liquid chromatography.

Kits

The present invention provides kits for treating liver cancer. For example, a kit may include one or more pharmaceutical compositions of safranal as described above. The compositions may be pharmaceutical compositions comprising a pharmaceutically acceptable excipient. In other embodiments involving kits, this invention provides a kit including safranal, optionally a TOP1 inhibitor, and optionally instructions for their use in the treatment of cancer. In still other embodiments, the invention provides a kits comprising one more pharmaceutical compositions and one or more devices for accomplishing administration of such compositions. For example, a subject kit may comprise a pharmaceutical composition and catheter for accomplishing direct intraarterial injection of the composition into a cancer. In an embodiment, the device is an intraarterial catheter. Such kits may have a variety of uses, including, for example, therapy, diagnosis, and other applications.

In Vitro Studies

The molecular mechanism by which safranal imparts its anticancer activity against liver cancer in vitro was explored by investigating the effects of safranal treatment on general aspects of HepG2 cells, such as cell viability, morphology, survival, and cell cycle progression. For the first time, safranal's role in promoting DNA damage through inducing DNA double-strand break (DSB) and inhibiting DNA repair mechanisms was demonstrated. Apoptosis was induced upon safranal treatment, which was evident from Flourescence Activated Cell Sorting (FACS) analysis data and activation of both initiator and executioner caspases. Finally, the present results provided evidence that the herein reported safranal-induced apoptosis was mediated through endoplasmic reticulum (ER)-stress.

Safranal Inhibits Growth and Survival of HepG2 Cells

To assess the cytotoxic effects of safranal (FIG. 1A) on liver cancer in vitro, HepG2 cells were treated with a range of concentrations (50-900 µM) of safranal for 24, 48, and 72 hours. Treatment with safranal resulted in dose- and time-dependent inhibition of cellular viability ($IC_{50}$ 500 µM; FIG. 1B). Cells treated with increasing doses of safranal for 24 hours exhibited morphological alterations including more rounded cell shapes, cell shrinkage, and increased detachment. Safranal-induced morphological changes were particularly evident after treating cells with a dose of 500 µM (FIG. 1C). Colony formation assay was also performed to assess the effects of safranal on the survival of HepG2 cells. Cells were treated with a range of concentrations (30-100 µM; higher doses eradicated all colonies) of safranal.

FIG. 1D provides representative images of a colony formation assay of HepG2 cells treated with the different concentrations of safranal after 24 hours. The effects of safranal treatment were quantified by calculating percent of area occupied by colonies in treated and non-treated samples (representative of triplicate samples) and absorbance of each treated and non-treated wells (representative of biological triplicates, each in technical triplicate). T-test was carried out (* p≤0.05,  p≤0.001, *p≤0.0001). Safranal inhibited colony formation of HepG2 cells in a dose-dependent manner, being most effective at 100 µM dose. This inhibition was clearly reflected by the lower number of visible colonies in the treated plates in comparison to the control. The decreasing numbers of colonies was quantitatively represented in smaller occupied areas and lower optical densities.

Safranal Arrests HepG2 Cells at G2/M and S Phase and Affects Cell Cycle Regulators To investigate how safranal affects cell cycle progression, cell cycle distribution was analyzed by flow cytometry. Treatment with 500 µM safranal resulted in a G2/M phase arrest at 6 and 12 hours post treatment, and an S-phase arrest at 24 hours. Additionally, safranal induced significant (p<0.001) increase in sub-G population post 24 and 48 hours of treatment, indicating that safranal induced apoptosis of HepG2 cells (FIG. 2A).

The effect of safranal on the protein expression of key cell cycle regulators was investigated where HepG2 cells were treated with 500 µM safranal for 6, 12, 24, and 48 hours. Expression of phosphorylated histone H3, an indicator of cells entering mitosis, was inhibited dramatically post safranal treatment, suggesting interruption of G2/M transition, which is also reflected in the inhibition of the proliferation marker PCNA (FIG. 2B). Cdc2/Cyclin B1 (also known as Cdk1/Cyclin B1 complex) is needed for G2/M transition and has been shown to require CDC25B for its activation in vitro [16]. Interestingly, safranal was shown here to inhibit Cdc2 expression starting at 12 hours while inhibiting expression of Cyclin B1 and CDC25B starting at 6 hours of treatment. To further understand the mechanism by which safranal exerts its effects on the corresponding CDC25B, a molecular docking approach was utilized with the aim of identifying the most probable binding mode and type of interactions taking place in such complex. Interestingly, safranal showed a binding profile in which the aldehyde carbonyl group involved in strong H-bond interaction with the catalytic Arg-482 of CDC25B (FIG. 2C) suggesting a direct interaction between safranal and CDC25B.

Safranal Exerts its Cytotoxic Effect Through Modulating the DNA Repair Machinery The S-phase arrest shown by FACS analysis 24 hours post safranal treatment was associated with the expression of p53, an indicator of DNA damage (FIG. 3A). Key markers of DNA replication, proliferation, and DNA damage were thus investigated to understand the effect of safranal on these processes. p-H2AX (DNA damage marker) is normally recruited to DNA break sites to form nuclear foci17 in cells experiencing DNA damage resulting in cell cycle arrest at G2. Interestingly, H2AX expression remained unchanged upon treatment with safranal, whereas p-H2AX was observed starting at 6 hours post safranal treatment (FIG. 3A), which is in line with data reported herein of safranal-induced G2/M arrest at 6 and 12 hours. Failure to repair DNA lesions has been shown to deregulate replication and transcription and lead to mutagenesis and apoptosis [18].

Topoisomerase I (TOP1) plays a key role in DNA replication and its inhibition may lead to DNA damage which can be protected by tyrosyl-DNA phosphodiesterase (TDP1) in complex with PARP. HepG2 cells treated with safranal for 6, 12, 24, 48 hours expressed higher levels of TOP1 and lower levels of TDP1, starting at 6 hours (FIG. 3A). Repair of DSB is also known to be mediated by HDAC1 and HDAC2 activities. Safranal's effect on HDAC1 expression was clear; however, the expression of HDAC2 remained unchanged. Additionally, a molecular docking experiment revealed direct interaction between safranal and the corresponding TDP1 active site (FIG. 3B). As FIG. 3C shows, pre-incubation of the cells with safranal for 24 or 48 hours before topotecan greatly enhanced the cytotoxic effects of topotecan on HepG2 cells. The topotecan IC50 is reduced from 0.118 µM to 0.0016 upon incubation of the cells with safranal for 24 or 48 h before topotecan, with a sensitization factor of 73, as reported below in Table 1:

19

TABLE 1

| IC50 of topotecan ± safranal | | |
| --- | --- | --- |
| Treatment | IC50 (μm) | Sensitization Factor |
| Topotecan alone | 0.118 | |
| Safranal (24 h) + Topotecan | 0.0016 | 73 |
| Safranal (48 h) + Topotecan | 0.0016 | 73 |

Safranal Induced Apoptosis of HepG2 Cells

Studying the effects of safranal (500 μM) on the progression of HepG2 cells through the cell cycle demonstrated a fraction of subG1 cells in the histogram indicative of apoptosis. The fraction of subG1 cells was 6.3% after 24 hours and increased to 26.2% after 48 hours of safranal treatment compared to 0.9% in control cells treated with DMSO (FIG. 4A). To confirm the induction of apoptosis in HepG2 cells after treatment with safranal, annexin V binding assay was employed and resulted in a significant (p<0.01) increase in the number of dead cells from 8 to 31% after 48 hours (FIGS. 4A, 4B). To study the effect of safranal on apoptosis, changes in expressions of Bax (pro-apoptotic), Bcl-2 (anti-apoptotic), of initiator caspases (caspase-8 and -9) and of executioner caspases (caspase-3 and -7) were investigated. The ratio of Bax to Bcl-2 increased post safranal treatment in a time-dependent manner (FIG. 4C). In addition, caspase-8 was cleaved starting at 24 hours, whereas caspase-9 was cleaved starting at 12 hours post safranal treatment, which corresponds well with the aforementioned markers of induced DNA damage (FIG. 4D). Consistently, the activity of executioner caspases-3 and -7 increased following safranal treatment (FIG. 4E). Upregulation of pro-apoptotic proteins and the induced activity of caspases correlate well with the annexin V analysis of apoptosis.

DEG of Safranal-Treated HepG2 Cells is Exposure-Time Dependent

To interrogate how HepG2 cells respond to treatment with safranal at the system level, cells were treated with safranal for 6, 12, 24, and 48 hours, and the RNA isolated from biological triplicates were subjected to transcriptome sequencing. Following quantification of the obtained results from each sample (triplicates), differentially expressed genes (DEGs) were identified with a fold change threshold of ≥0.58 log 2 value (or 1.5 fold) with FDR-adjusted p-values at 0.05. The accuracy and reproducibility of the RNAseq quantification was validated by real-time PCR (qPCR) as shown.

How the safranal-treated HepG2 cells expression profiles change in comparison to the controls over time was investigated by using the short time-series expression miner (STEM) analysis algorithm. The STEM clustering tool created 50 model profiles and determined which profiles had a statistically significant value by using 50 permutations per gene with standard hypothesis testing. Significant model profiles also grouped together based on similarity to form clusters of significant profiles (data not shown). Of the 50 profiles, 14 showed statistically significant profiles. Of those, we focused on up- and downregulated trends after safranal treatment. STEM also provides gene ontology (GO) analysis for each cluster; enriched GO terms for genes displaying downregulated trend were cell division and DSB repair. In addition, the up-regulated trend was enriched in positive regulation of protein ubiquitination and regulation of response to DNA damage stimulus.

The distribution of DEGs from safranal treatment with selected time points (12 and 24 hours) was obtained relative to the control (untreated) sample. A total of 6,581 genes were significantly differentially expressed at 12 hours, and 7,789 genes at 24 hours. Of these time points 2,812 and 2,458 genes were upregulated respectively, and 3,769 and 5,331 were downregulated (FIG. 5). The numbers of DEGs uniquely appearing at 12 hours posttreatment were 1,506 (upregulated) and 1,092 (downregulated), while 1,248 (upregulated) and 2,558 (downregulated) genes were uniquely appearing in the 24 hours. These results suggest that the differentiation of expressed genes is time-dependent, and there are more differentially expressed transcripts when cells are treated with safranal for 24 hours as compared to 12 hours. We found many common genes overlapping between the two time points. In addition, there were 118 genes that were upregulated at 12 hours then downregulated at 24 hours; these genes were mainly involved in G1/S transition of mitotic cell cycle and cell division. Only 22 genes were, however, downregulated at 12 hours then upregulated at 24 hours and those were involved in proteolysis and regulation of cyclin-dependent protein serine/threonine kinase activity. These findings are collectively consistent with present immunoblot results that show safranal's effects on cell cycle progression through inhibition of Cdc2, Cyclin B1, and CDC25B; and induction of p53.

DEGs of Safranal—Treated HepG2 are Enriched in GO Terms Related to DNA Damage, Cell Death, and Response to Unfolded Protein Gene ontology (GO) and gene set enrichment analyses Gene ontology (GO) and gene set enrichment analyses were carried out for all DEGs with respect to biological processes using XGR software. As XGR integrates enrichment and network analyses based on input gene sets, here we focused on enrichment terms involved in cell cycle, DNA damage and other relevant pathways (Table 2). A number of up-regulated genes in 12 hours safranal treatment were enriched in GO terms related to cellular response to DNA damage stimulus, proteasome-mediated ubiquitin-dependent protein catabolic process, and unfolded protein response (UPR), (Table 2). We also detected a number of downregulated genes for 12 hours safranal treatment enriched in GO terms related to cell migration, growth, and wound healing. For the up-regulated genes in 24 hours safranal treatment, the enriched GO terms were related to proteasome-mediated ubiquitin-dependent protein catabolic process, UPR, and apoptotic mitochondrial changes. While for the downregulated genes for the same treatment, the enriched GO terms were related to signal transduction, cell adhesion, and wound healing, as reported in Table 2:

TABLE 2

| Summary of relevant GO enrichment for up- and downregulated genes after 12 and 24 h treatment. | | |
| --- | --- | --- |
| Term Name | N | FDR |
| Upregulated 12 h | | |
| Cellular Response to DNA damage stimulus | 48 | 0.000024 |
| Proteasome-mediated ubiquitin-dependent protein catabolic process | 47 | 0.000059 |
| Response to unfolded protein | 14 | 0.0008 |
| Downregulated 12 h | | |
| Cell migration | 28 | 0.0071 |
| Growth | 27 | 0.026 |
| Wound healing | 25 | 0.0031 |

TABLE 2-continued

Summary of relevant GO enrichment for up- and downregulated
genes after 12 and 24 h treatment.

| Term Name | N | FDR |
|---|---|---|
| Upregulated 24 h | | |
| Proteasome-mediated ubiquitin-dependent protein catabolic process | 50 | 9.6E−10 |
| Response to unfolded protein | 12 | 0.00074 |
| Apoptotic mitochondrial changes | 6 | 0.0053 |
| Downregulated 24 h | | |
| Signal transduction | 327 | 0.00011 |
| Cell adhesion | 149 | 0.00083 |
| Wound healing | 32 | 0.0037 |

We then used the manually-curated, knowledge-based Ingenuity Pathway Analysis (IPA) designations to introduce functional relevance to up- and downregulated genes after safranal treatment for 12 and 24 hours. Among the IPA generated top enriched networks were liver hyperplasia/hyper-proliferation, hepatocellular carcinoma, liver prolif-eration, liver necrosis/cell death and liver regeneration. The resulting networks indicated the inhibition of "hepatocellu-lar carcinoma" at both 12 and 24 hours after safranal treatments (data not shown).

Safranal Induces ER Stress in HepG2 Cells through Upregu-lation of Unfolded Protein Response To further explore the functions associated with differen-tially regulated genes, we identified the top 50 up- and downregulated genes at both 12 and 24 hour time points, which are displayed in a heatmap (FIG. 6A). In addition, we identified the top 100 up- and downregulated genes at both 12 and 24 hour time points. To carry out gene set enrichment and KEGG pathway analysis, we use BiNGO and XGR to identify the enrichment terms (data not shown). Results from the GO network show that majority of the up-regulated genes in safranal-treated HepG2 for 12 and 24 hours are involved with UPR (FIGS. 6B, 6C). Assessment of ER regulators was carried out to confirm if HepG2 cells were experiencing ER stress and UPR upon treatment with safra-nal at different time points. The main sensors of UPR, PERK, IREL and ATF6 exhibited a general upregulation trend. Downstream CHOP/DDIT3 and phosphorylated eIF2a were also upregulated post safranal treatment in a time-dependent manner. Moreover, expressions of GRP78, the master UPR regulator, and of p27 were induced post safranal treatment; whereas the expression of p21 was inhibited post safranal treatment (FIG. 7).

Discussion

Saffron and its derivatives have long been known for their capacity to impede both cancer initiation and promotion as well as promoting cancer therapy. They have also been shown to possess antitumorigenic and proapoptotic activi-ties in vitro. In the present study, safranal significantly inhibited proliferation of HepG2 at 500 μM. In other studies, safranal has shown potent inhibitory effect at lower doses [11,12,19] suggesting that HepG2 cells might be more resistant to safranal. Many studies have reported the selec-tive toxicity of saffron extract and its derivatives against cancer cells and its non-existent toxicity against normal cells [21].

The ability to form colonies is essential for cancer cells survival and proliferation, where several studies have reported the ability of pro-apoptotic natural products to inhibit colony formation in different cancers [22-24]. Here too, safranal reduced the colony-forming ability of HepG2 cells in a dose-dependent manner.

Dysregulation of components of the cell cycle machinery is the common denominator of human cancers. Cancer cells often evade cell cycle checkpoints to avoid cell cycle arrest and/or apoptosis. Progression from G2 to M phase requires the formation of Cdc2 and Cyclin B1 complex, through the activity of CDC25B [16]. Indeed, inhibiting CDC25B impaired checkpoint recovery and arrested the cell cycle at the G2 phase [25]. In line with those studies and consistent with the aforementioned safranal-induced cell cycle arrest and drop in p-histone H3 level, safranal dramatically inhib-ited the expression of Cyclin B1 and CDC25B protein expression. Interestingly, in silico docking analyses revealed an interaction between safranal and the catalytic Arg-482 of CDC25B (FIG. 2C), suggesting that G2/M phase arrest of safranal-treated HepG2 cells might have been due to dis-ruption of protein-protein interaction between CDC25B and Cdc2/Cyclin B1 complex. Lund et al. [26] demonstrated inhibition of CDC25B by 2-fluoro-4-hydroxybenzonitrile through binding to a pocket in the vicinity of a protein-protein interaction hot-spot, rather than CDC25B catalytic site [26]. This is particularly intriguing as discovering or designing de novo inhibitors of CDC25B is quite challeng-ing due to its shallow active site pocket [27]. However, a number of natural and synthetic compounds that show selective inhibition of CDC25B have shown promising anticancer effects in several cancers [28]. Some of those compounds displayed inhibitory effects against parental cancer cell line and their multidrug-resistant derivatives [29,30]. Other inhibitors were reported to block cell cycle progression of different cancer cells; and interestingly, some were able to inhibit cell cycle progression at both G1 and G2/M phases [28]. In agreement with those findings, safra-nal did inhibit cell cycle progression, through arresting HepG2 cells at both S and G2/M phases. Similar findings have been reported where UCN-01, a protein kinase inhibi-tor, inhibited proliferation of hepatoma cell lines including HepG2 through arresting the cell cycle at S and G2/M phase [31].

Safranal treatment induced phosphorylation of histone H2AX that is a marker of DSB, also induced by replication stalling [32]. The elevation of p-H2AX coincided with a drop in TDP1 level suggesting that DNA breaks may result from lack of repair by TDP1. To understand how safranal induces DNA damage, we investigated a key regulator of DNA replication (TOP1) and other contributors to DNA damage repair (TDP1, PAPR, HDAC1 and HDAC2). TOP1 facilitates DNA replication by relieving supercoiling and tension of DNA via cleaving and rejoining one strand of the DNA duplex. Thus, TDP1, through forming a multiprotein complex that includes PARP33, is normally needed to remove TOP1-DNA cleavage complexes, thus protects against DNA strand breaks arising as a result of TOP1 malfunction. Cancer cell survival relies on accurate DNA repair, which provides an opportunity to treat tumors by DNA damaging agents. Cleaving PARP results in impairing DNA repair and accumulation of DNA damage. Similarly, as a key component in the DNA repair machinery, TDP1 inhibition can accentuate the effects of DNA damaging agents and ultimately apoptosis. This is particularly critical when developing novel therapeutic agents against cancer. DNA damage arising from conventional cancer therapy (e.g. chemotherapy and radiation) is recognized by DNA repair machinery of cancer cells which leads to drug resistance

[34]. By inhibiting TDP1 and hindering DNA repair, more effective cancer therapeutics can be developed [35]. TDP1 inhibitors are scarce and only few are effective at inhibiting TDP1 expression at micromolar concentrations [36]. Here, 500 μM of safranal inhibited TDP1 expression starting at 6 hours; despite the increase in the expression of TOP1. The present in silico docking analysis revealed an interaction between safranal and the TDP1 active site. The human TDP1 consists of two domains, namely; the N-terminal domain (residues 162-350) and C-terminal domain (residues 351-608). The active site is located between these two domains and consisted from the catalytic residues (His-263, Lys-265, His-493, Lys-495 and Asn-516). Safranal showed strong interaction pattern within the TDP1 active site where it interacted with key resides such as; Lys-495, Asn-516 and Ser-399 located at the C-terminal (FIG. 3B) suggesting an inhibitory role of safranal on TDP1 protein expression. In addition, SRB assay revealed an increased sensitivity of safranal-treated HepG2 cells to topotecan, which may indicate that pre-incubation with safranal inhibited TDP1 that is needed for the repair of topotecan-induced TOP1-DNA adducts (FIG. 3C). HDAC1 and HDAC2 participate in the DNA damage response, where they facilitate repair of DSB37. Indeed, cells that were HDAC1 and HDAC2 depleted have been shown to be hypersensitive to DNA-damaging agents, suggesting a defective DSB repair [37]. Safranal inhibited the expression of only HDAC1, whereas HDAC2 expression remained unchanged.

Unresolved DNA damage arising from DNA replication may trigger apoptosis [38]. When a progressing replication fork encounters unrepaired DNA damage such as single- or double-strand breaks, this leads to replication fork arrest, which may collapse the replication fork and favor cell death via apoptosis. In the present study, safranal-induced apoptosis was clearly demonstrated by the detection of subG1 cells in the cell cycle distribution, the binding pattern to annexin V, and the increased Bax/Bcl-2 ratio. Mammalian caspases are divided into initiator (caspase-8 and 9) and executioner (caspase-3, 6, 7) caspases; where the former activate the latter that leads to the proteolysis of key structural proteins and then to apoptosis (intrinsic and/or extrinsic pathways) [39].

We explored if the intrinsic apoptosis pathway, frequently mediated by DNA damage, was activated upon safranal treatment. Indeed, safranal induced cleavage of caspase-9, the initiator of the intrinsic pathway, in a time-dependent manner. Interestingly, safranal also induced cleavage of caspase-8, the initiator of the extrinsic pathway, in a similar manner to caspase-9. Other natural products and derivatives have shown similar pro-apoptotic activates by activating both pathways [40-42]. Activation of both caspases 8 and 9, has been involved in apoptotic pathway activation by endoplasmic reticulum (ER) stress [43,44]; a process that safranal modulates and will be discussed later. As expected, safranal-induced activation of the initiator caspases-8 and 9 resulted in the activation of executioner caspases-3/7 and ultimately led into induction of apoptosis in HepG2 cells.

To gain a significant insight into the mechanism of safranal's anticancer effects against HepG2 cells, we utilized a systems biology approach to analyze how safranal functions not only on the gene/protein level, but also on pathways and network levels. To further understand how safranal affects gene expression of HepG2 cells over time, we explored how the treatment profiles change in comparison to the untreated control over time using STEM clustering algorithm. Out of 50 model profiles created by STEM algorithm, 14 profiles showed statistically significant values, profiles 0 and 4, exhibiting a downregulation trend, were enriched in GO terms related to cell division and DSB repair. This is consistent with immunoblot data showing inhibition of PCNA, TDP1, HDAC-1 and 2; and cleavage of PARP. On the other hand, profiles 35 and 36, exhibiting an upregulation trend, were enriched in GO terms related to positive regulation of protein ubiquitination, and regulation of DNA damage response (data not shown). Ubiquitin and its related gene products carry out their functions through covalent attachment to cellular proteins, thereby changing the stability, localization, or activity of the target protein [45]. The identified up-regulated genes encoding ubiquitin-conjugating enzymes included UBE2A, UBE2B, UBE2D1 and F-box protein 7 (FBXO7). Those enzymes mediate the ubiquitination of the proteins involved in cell cycle and lead to proteasomal degradation of target proteins.

We then focused on enriched terms involved in cell cycle, DNA damage and other relevant pathways (Table 2). Several up-regulated genes at both 12 and 24 hours, were enriched in GO terms related to UPR while up-regulated genes after 12 hours of safranal treatment were enriched in GO terms related to cellular response to DNA damage stimulus; which correlates well with the findings reported herein showing an increase in DNA damage markers post safranal treatment. Down-regulated genes after 12 hours of safranal treatment were, however, enriched in GO terms related to growth, wound healing and cell migration. Indeed, by inhibiting cell growth, cell migration, and wound healing, survival and development of safranal-treated HepG2 cells can be impaired. A similar pattern was demonstrated after 24 hours of safranal treatment. In addition, pathway analyses revealed the regulatory networks associated with the list of differentially expressed genes (DEGs) after 12 and 24 hours of safranal treatment. HCC was highlighted as one regulatory network among the top networks that fit with our set of DEGs at 12 and 24 hours (data not shown). More than 200 genes were associated with the HCC network. We focused on a group of genes that are associated with of DNA damage repair, cell cycle progression, proliferation, apoptosis, ER stress, growth and invasion. The resulting networks predicted the inhibition of HCC at both 12 and 24 h after safranal treatments through inducing DNA damage response (e.g. p21/CDKN1A) and interrupting DNA repair (e.g. MGMT), in addition to inhibiting proliferation, survival, and invasion (e.g. MET, TERT, MMP2, MMP9).

Gene set enrichment and KEGG pathway analysis of safranal-treated cells showed that the majority of the up-regulated genes were involved in UPR. Prolonged ER stress and UPR often lead to the accumulation of pro-apoptotic regulators, which then activate the cell death pathway [46].

To prevent prolonged ER stress and subsequently cell death, cells restore the ER function through the activity of stress sensors, ATF6, IREL and PERK [47]; all of which fall under the regulation of the main ER resident chaperone GRP78/BiP [48]. Safranal treated HepG2 exhibited an overall upregulation of ER stress sensors and induced GRP78 expression consistent with reported effects of common pharmaceutical ER stress inducers (e.g., tunicamycin and thapsigargin) [49]. Safranal also increased p27 protein levels in treated cells. P27 is upregulated under ER stress conditions to block cell cycle progression and induce growth arrest [50,51]. In contrast, safranal inhibited p21 protein levels in HepG2 treated cells. Under ER stress, p21 is suppressed which sensitizes cells to DNA damage-induced apoptosis, shifting from the pro-survival to the pro-apoptotic role of UPR [52,53]. In addition, safranal treatment upregulated expression of CHOP and phosphorylated eIF2a. CHOP is involved in ER stress-mediated apoptosis, where overexpression of CHOP results in cell cycle arrest and apoptosis [54]. Phosphorylated eIF2α is also involved in ER stress response, where phosphorylation of eIF2α inhibits protein synthesis upon apoptotic stimuli [55]. Pharmacological induction of ER stress has been shown to suppress p21 levels, concurrent with induction of CHOP, a major regulator of ER stress-related apoptosis. CHOP was, therefore, reported to mediate cell cycle through regulating p21/waf1 during ER stress driving cells into a pro-apoptotic program manifesting its dual function where in addition to inherently inducing apoptosis, CHOP also relieves the anti-apoptotic activity of p2153. Curcumin has been reported to inhibit ERAD activity and upregulate PERK, eIF2α, and CHOP; which sensitizes APL cells to UPR-induced apoptosis56. Similar effects have been reported in U266 and HepG2 cells, where treatment with anacardic acid resulted in ER stress-induced apoptosis, in time- and dose-dependent experiments [57]. Treatment with anacardic acid increased expression of ATF4, p-eIF2α, GRP78, and CHOP, suggesting that ATF4 is one of the key pathways promoting anacardic acid mediated ER stress. These data are consistent with observations made in our study, where p-GRP78 and CHOP protein levels increased post safranal treatment, in addition to activation of upstream pathways (PERK/p-eIF2α) that promote translation of ATF458; suggesting that safranal-induced ER stress could also be partially mediated through ATF4 pathway or by inhibiting the ER function in general. Persistent ER stress has been shown to activate caspase-8 which in turn activates caspase-9 and mediate apoptosis [59,60]. Biological and pharmacological ER stressors have been shown to activate caspase-861. ER stress inducers can be utilized in therapeutic approaches [62] and some are already being used clinically or undergoing preclinical assessment [63-65].

In conclusion, the present study provides evidence that safranal exerts its anticancer effect in HepG2 cells by inhibiting DNA repair, resulting in increased DNA damage. This notion is evident in safranal inhibition of TDP1, a strong contributor to the DNA DSB repair mechanism, as revealed by molecular docking, immunoblotting, and SRB assay. Safranal also induced cell cycle arrest, which is reflected in inhibition of histone-H3 phosphorylation, downregulation of Cyclin B1 and Cdc2. Prolonged safranal-induced ER stress may explain the activation of both initiator caspases (caspase-8 and -9), which leads to activation of executioner caspase-3 and -7, PARP cleavage and apoptosis. These findings were consistent with systems analysis where UPR is among the top GO terms of up-regulated genes in response to safranal treatment for 12 and 24 h. Taken together, results reported herein suggest a novel mechanism of antiproliferative activity of safranal against HepG2 liver cancer cells that relies on ER stress and UPR activation (depicted in FIG. 8).

Methods

Cell culture. Cells of liver cancer cell line, HepG2, were cultured in RPMI 1640 medium (HyClone) supplemented with 10% fetal bovine serum (Sigma Aldrich) and containing 1% of 100 U/ml penicillin and 100 μg/ml streptomycin (Sigma Aldrich) at 37° C. in a humidified 5% $CO_2$ atmosphere. Cells were sub-cultured each 3-5 days using trypsin 0.25% (Hyclone).

MTT assay. HepG2 cells were seeded at a density of 5000 cells/well in 96-well plates in 100 μL of complete growth medium. Cells were allowed to attach before being treated with different concentrations of safranal (Sigma Aldrich) (50 μM, 100 μM, 500 μM, 700 μM and 900 μM) for 24, 48 and 72 hours. After which, the cells were treated with 3-[4,5- dimethylthiazol-2-yl]-2,5-diphenyltratrazolium bromide (MTT) (Sigma Aldrich) and incubated for 3 hours. The formed formazan crystals were dissolved using DMSO and the absorbance of the resulting product was measured at 570 nm using an Epoch microplate spectrophotometer (BioTek). Cell viability is presented as percentile of the untreated control which was calculated accordingly: Percent of viable cells=(Abs. of treated cells/Abs. of control cells)×100. *p≤0.05, p≤0.001, *p≤0.0001.

Cell morphology. HepG2 were seeded at a density of 0.25×106 cells/well in 6-well plate. After allowing the cell to attach, HepG2 cells were treated without or with different concentrations of safranal (30, 50,100, 500,700 μM) for 24 hrs. After which, cells were fixed and stained with crystal violet. The morphology of the cells was assessed after being fixed and stained with 0.5% crystal violet using IX53 microscope (Olympus).

Colony formation. HepG2 cell were seeded at a density of 1000 cells/6-well plate, and left to incubate for 24 hours to allow attachment before being treated with different concentrations of safranal (30, 50, 100 μM) for 24 hours. After which, culture media containing safranal was replaced by fresh growth media without safranal. Culture media was replenished every 3 days, until visible colonies were formed. Colonies were fixed with absolute methanol, then stained with 0.5% crystal violet. Colonies were then imaged and analyzed using ImageJ plugin ColonyArea. Results are represented as the percent of area occupied by colonies. To confirm, an absorption-based method was carried out to validate results obtained from ImageJ. Briefly, stained colonies were treated with 10% acetic acid solution to dissolve the crystal violet stain. After which, 100 μL of each triplicate sample was transferred to a 96-well plate (in triplicates), and absorbance was measured using an Epoch microplate spectrophotometer (BioTek). *p≤0.05, p≤0.001, *p≤0.0001

Cell cycle analysis. HepG2 cells were seeded at density of $3×10^6$ cells per flask in complete growth medium and were allowed to attach overnight. After which, cells were treated with 500 μM of safranal for different time intervals (6-48 hours). At the indicated time intervals, cells were collected by incubation with trypsin and washed twice with PBS. Collected cells were fixed in 70% ethanol, treated with RNase and stained with propidium iodide. Cell cycle distribution was analyzed by flow cytometry in a FACS scan (Becton Dickenson, Germany).

Western blotting. HepG2 cells were seeded at a density of $1×10^6$ cells/100 mm plate and allowed to attach before being treated with safranal. Cells were treated with 500 μM of safranal for different time intervals (6-48 hours) for time-dependent experiments. Whole cell lysates were separated using 10-15% SDS polyacrylamide gel electrophoresis. Proteins were transferred onto PVDF membranes prior to incubation with various primary antibodies p-histone H3, Cdc2, Cyclin B1, CDC25B, p21, p53, H2AX, p-H2AX, TOP1, TDP1, Cleaved PARP1, PCNA, HDAC1, HDAC2, Cleaved Caspase-9, Cleaved Caspase-8, Bax, Bcl-2, GRP78, ATF6, IRE1, PERK, p-eIF2S1, p2'7, and CHOP. GAPDH, β-actin, and α-Tubulin were used as loading controls. Protein bands were detected using WesternSure Chemiluminescent Substrate (LI-COR) and C-DiGit blot scanner (LI-COR).

Caspase-3 and 7 activities. HepG2 were seeded at a density of 5000 cells/well in a 96-well plate, and were allowed to attach. After which, cells were treated with 500 and 700 μM of safranal for 24 hours. Caspase-3 and 7 activities were detected using CaspaseGlo® 3/7 Assay kit according to manufacturer instructions (Promega). Luminescent signal was detected using GloMax Discover System (Promega).

Molecular docking. The program Autodock Vina was employed during all the docking experiments. An X-ray crystal structures for the target macromolecules namely; CDC25B and TDP1 were obtained from the RSCB protein data bank under the entry codes of 1QB0 and 1NOP, respectively. Subsequently, the complexed inhibitors and water molecules were extracted from the initial X-ray structures and polar hydrogens and Gastieger charges were generated using the MGL Tools. Safranal was drawn using the software ChemDraw Ultra 8.0 (Cambridge Soft Corporation, USA) and was optimized for energy and geometry using MMFF94 force field. Initially, a grid boxes were established to cover the desired target molecule with a spacing of 1.0 Å between the grid points. Later, 20 $\text{Å}^3$ CDC25B box was centered toward the coordinates of (17.302 X, 8.987 Y, 13.268 Z), and a 14 $\text{Å}^3$ TDP1 box was centered toward the coordinates of (6.387 X, 53.857 Y, 3.796 Z). The exhaustiveness and the number of poses were set to 12 and 10 respectively. Finally, results visualization and the 3D-best docked poses were achieved using the PyMOL molecular viewer (Schrödinger Inc., USA).

SRB assay. The effect of safranal on the cytotoxicity of the topoisomerase 1 inhibitor topotecan was tested using the sulforhodamine-B (SRB) assay as previously described [66]. Exponentially growing HepG2 cells were seeded in 96-well plates at cell density of $1 \times 10^4$ cells per well. After overnight incubation, cells were treated with topotecan alone (0, 0.01, 0.1, 1, 10 and 100 μM) for 48 hours or with safranal IC50 (500 μM) for 24 hours followed by topotecan for 48 hours, or with safranal IC50 (500 μM) for 48 hours followed by topotecan for 48 hours. At the end of the incubation period, cells were fixed with 50% trichloroacetic acid (TCA) for 1 hours at 4° C. followed by washing, staining with SRB for 30 min followed by washing and solubilization of the stain with 10 mM Tris base (pH 10.5). The optical density (OD) at each well was measured spectrophotometrically at 564 nm with an ELISA microplate reader (Metertech. S960, USA). The IC50 values were calculated using sigmoidal concentration-response curve fitting models (Graph Pad, Prizm software).

RNAseq libraries construction and sequencing. Total RNA was isolated from three biological replicates of safranal treatments and untreated sample using RNeasy Mini Kit (Qiagen) following the manufacturer's instructions. The RNAseq libraries were prepared using TruSeq RNA sample prep kit (Illumina, Inc.) following the manufacturer's instructions. Briefly, TruSeq RNA sample prep kit converts the poly-A containing mRNA in total RNA into a cDNA library using poly-T oligo-attached magnetic bead selection. Following mRNA purification, the RNA is chemically fragmented prior to reverse transcription and cDNA generation. The fragmentation step results in an RNAseq library that includes inserts that range in size from approximately 100-400 bp. The average insert size in an Illumina TruSeq RNA sequencing library is approximately 200 bp. The cDNA fragments then go through an end repair process, the addition of a single 'A' base to the 3' end and then ligation of the adapters. Then, the products are purified and enriched with PCR to create the final double stranded cDNA libraries. Finally, libraries quality control and quantification were performed with a Bioanalyzer Chip DNA 1000 series II (Agilent) and sequenced directly using the high-throughput Illumina HiSeq sequencing system (Illumina, Inc.).

Alignment and analysis of Illumina reads against the reference genome. The data was processed through the standard RNAseq analysis pipeline at NYUAD. Briefly, alignments were performed using tophat2 v2.1.0 with the parameters "-no-novel-junctions" and "-G" when specifying the genome file. Following the tophat2 alignment stage, read counts were generated using HTseq count, and the counts were analyzed using the DESeq2 R library. The reference genome and GFF annotation correspond to the *Homo sapiens* GRCh38.p2 genome version. Venn diagram summarizing the gene expression analysis was constructed using the web-based tool InteractiVenn. Heatmaps were produced by Excel.

Quantitative real-time PCR (qPCR). For qPCR, cDNA corresponding to 50 ng of total RNA was used per transcript to be quantified. Quantitative PCR reactions were performed on an Applied Biosystems StepOnePlus instrument system using KAPA SYBR FAST One-Step qRT-PCR Kit (Kapa Biosystems, USA) with gene-specific primers according to the manufacturer's instructions. Data were normalized relative to Hprt1 and Actb gene values, which exhibited stable expression levels between safranal treatments and the control samples. Melting curves were performed on the product to verify that only a single product was amplified without primer dimers and other bands; melting curve analysis was performed for each primer pair before further analyses. Relative quantitative analysis was performed by comparative quantitation using StepOne v2.3 software. All reactions were run in triplicate.

Differential gene expression trend analysis. To analyze the trend of gene expression profiling between control compare to treatment from four-time points based on FPKM values, Short Time-series Expression Miner (STEM) software was used to compare the trends exhibited in safranal treatment. P-values correspond to the differential gene expression test, which was performed to analyze all trends in these four-time points. STEM determines statistically significant gene expression profiles by comparing the ratios relative to the first time point (here is control). Thus, the first value is always 0. The STEM clustering method was selected with the default parameters; STEM determines profiles statistically significantly enriched by comparing the number of genes assigned with what would be expected based on permutation with Bonferroni correction for multiple comparisons.

Gene set enrichment analysis. Functional and gene set enrichment analysis of DEGs was performed using eXploring Genomic Relations (XGR) which is an open source tool for enrichment analysis with default parameters. The enrichment test is based on Hypergeometric distribution to identify the enriched gene ontology terms. The false positive rate was calculated by simulating a random set of genes of different sizes and found they were independent of the size of gene sets. Network analysis of over-representation GO terms was performed using the Biological Networks Gene Ontology tool (BiNGO) plug-in for Cytoscape. BiNGO retrieved the relevant GO Biological process annotation then tested for significance using the hypergeometric test and corrected multiple testing using Benjamini and Hochberg false discovery rate (FDR) correction≤0.05.

Pathway analysis. We used the Ingenuity Pathway Analysis (IPA) (QIAGEN Inc.) [67] to examine the biological network associated with the safranal treatment at 12 and 24 hours (data not shown). IPA software uses a manually curated database which contains information from several sources including published journal papers and gene annotation databases. The Fisher's exact test was used to calculate the probabilities between input gene set with the canonical pathway, disease and tox function. IPA also predicted the upstream and downstream effects of activation or inhibition on other molecules based on the input gene set's expression data.

In Vivo Studies

In vivo HCC model was successfully induced in male Wistar rats, then treated with sorafenib alone, safranal alone, and with both safranal and sorafenib. Data analysis showed the efficiency of safranal as a drug and an adjuvant in restoring liver function. Presented results also showed safranal's inhibitory role of cell cycle, and its proapoptotic capacity suggesting safranal's high potential as a novel anti-cancer drug.

Male Wistar rats, weighing around 160 gm, were used in this study. Rats were provided by the animal research facility at the College of Medicine and Health Sciences, United Arab Emirates University. Rats were housed under a 12-hour light/dark cycle at 24-26° C. They were maintained on a standard laboratory animal diet with food and water ad libitum.

Experimental Design

A modified version of the protocol described by DePeralta et al. (2016) and Schiffer et al. (2005) was used here to establish the hepatocarcinogenesis model. As seen in FIG. 9, animals were divided into five groups, each group having eight animals labelled as follows: control phosphate buffered saline (PBS), HCC, HCC+sorafenib, HCC+safranal, and HCC+safranal+sorafenib.

On the first 15 weeks, the control PBS group was treated with 1×PBS, whereas the experimental groups were given an intraperitoneal injection (IP) of 50 mg/kg of diethylnitrosoamine (DEN, Sigma Aldrich), a widely used chemical for inducing cancer, once a week. DEN was diluted with 1×PBS. Following a one-week break (week 16), the next three weeks (weeks 17 to 19) of treatment commenced. All drugs were administrated by oral gavage. All doses were chosen according to literature (Alsaied et al., 2014; Karafakioglu et al., 2017). For the HCC+sorafenib group, the drug (Carbosynth Limited) was administered at a dose of 10 mg/kg, five days a week. For the HCC+safranal group, the drug (Sigma Aldrich) was administered at a dose of 200 mg/kg, five days a week. For the HCC+safranal+sorafenib group, the drugs were administered at a dose of 200 mg/kg safranal+10 mg/kg sorafenib, five days a week. Both safranal and sorafenib were diluted with 1×PBS and drops of Tween 80. The oral LD50 of safranal is 5.53 mL/kg in male rats (Hosseinzadeh et al., 2013). After 24-hours from last treatment, the rats were euthanized by mild diethyl ether and dissected in equal conditions. Blood and whole liver were collected.

Blood Samples

Rats were euthanized then blood was collected by decapitation and processed for later investigation. The blood was collected in collection tubes (BD Vacutainer) and serum was separated by centrifugation at 1200×g for 10 minutes. Serum was collected and flash frozen immediately then stored at −80° C. for further analysis.

Biochemical Analysis

Alanine Transaminase (ALT), and Aspartate Aminotransferase (AST) assays were performed using commercial kits (Abcam), according to the protocol provided. ALT and AST activities were measured spectrophotometrically using Epoch by BioTek.

Liver Samples

Part of the liver was immediately flash frozen in liquid nitrogen then stored at −80° C. for further analysis. The other part was kept in 10% neutral buffered formalin at room temperature for histology.

Histopathological Examination

Liver sample specimens were fixed in 10% neutral buffered formalin, dehydrated in a series of graded ethanol, embedded in paraffin blocks, and cut into 3 μm-thick sections. To detect histopathological changes, sections were stained with hematoxylin and eosin (H&E), and reticulin stain kit according to the protocol provided (Abcam), then examined under light microscope (Ozkececi et al., 2016). Blinded examination of tissue samples was carried out by a pathologist from Tawam Hospital—United Arab Emirates.

Western Blotting

One hundredth gm (10 mg) liver was homogenized using 200 μl RIPA buffer (Sigma Aldrich) mixed with 2 μl protease inhibitor and 2 μl phosphatase inhibitor (Sigma Aldrich), and centrifuged at 4° C., 15,000 rpm for 15 minutes. Whole cell lysate was taken and stored at −80° C. Protein concentration was measured by Pierce BCA Protein Assay Kit with Promega GloMax Discover. A total of 35 μg of protein was loaded on a sodium dodecyl sulfate-polyacrylamide gel electrophoresis gel. The gel was then transferred to polyvinylidene difluoride membrane. The membrane was then blocked with 5% BSA in TBST for one hour at room temperature. Membranes were incubated with anti-Proliferating Cell Nuclear Antigen (PCNA), anti-PolyADP-ribose Polymerase (PARP), anti-caspase-3 (Cell Signaling Technology Inc.), anti-caspase-9 (Novus Biologicals), anti-Bax, anti-Bcl-2 (Santa Cruz), anti-Cdk1, anti-Cyclin B1, anti-Cdc25B (Cell Signaling Technology Inc.) over night at 4° C., then with HRP conjugated secondary, anti-mouse or anti-rabbit, antibody (Cell Signaling Technology Inc.) for one hour at room temperature. All primary and secondary antibodies were diluted in 5% BSA in TBST. Blots were incubated in WesternSure PREMIUM Chemiluminescent Substrate for antibodies' detection. Signal was visualized using Bio-Rad ChemiDoc XRS+ System. Band density and quantification was done using ImageJ (Amin et al., 2011). Total protein was used as a loading control and stained using SYPRO Ruby protein gel stain according to the protocol provided (Thermo Fisher Scientific) (Aldridge et al., 2008; Hu et al., 2016).

Total Protein as a Loading Control

Due to technical reasons, total protein was used in this study as the loading control instead of the other common markers like GAPDH, β-tubulin, and β-actin. A study published in 2003 used liver samples from normal, cirrhotic, and HCC tissues to inspect the housekeeping genes. Ten internal controls were used, and their expressions were determined using RT-PCR. Results showed that all internal control genes varied more than a 2-fold, and the commonly used genes like GAPDH and β-actin varied from 7- to 23-fold, precisely in tumor tissue (Kim & Kim, 2003). Following studies then tried to find an alternative way for this issue. Total protein, depending on the amount of total protein rather than a single protein, served as a better control for colorectal cancer and HCC compared with different common housekeeping proteins. Also, testing the signal's linearity with the loading amounts was preserved in total protein, while in the other housekeeping proteins it was lost (Aldridge et al., 2008; Hu et al., 2016). Due to technical problems with all common internal controls, a protocol that was mentioned by Aldridge et al. (2008) and Hu et al. (2016) was followed.

Results

Several enzymes are released from hepatocytes into the blood and are measured in the blood serum to test the efficiency of liver function, ALT and AST are the most common enzymes. The more severe the liver is damaged, the higher their serum levels get. Together, they are considered the best markers for liver injury (Liu et al., 2012). In addition to serum, the whole liver tissues were collected and properly stored for further histological and immunoblotting analyses. In histological examination, liver tissues were processed and stained for final imaging using the microscope (Martin, 2015). To detect markers of specific pathways, selected proteins were targeted using western blotting.

Biochemical Analysis

As shown in Table 3, ALT (P<0.01) and AST levels were elevated in HCC group as compared to control group, thus indicating liver damage. Treatment with safranal and with both safranal+sorafenib significantly (P<0.01) decreased ALT levels in the treated groups as compared to HCC group. Safranal and the combination therapy caused a significance decrease (P<0.05) as compared to sorafenib alone (HCC+ sorafenib). Values are expressed as mean±SEM of six rats per group (n=6). Activity is expressed as mU/ml for ALT and AST. Significance was determined using Microsoft Excel Data Analysis Tool Pack, t-test: two-sample assuming equal variances (a versus PBS, b versus HCC, c versus HCC+ Sorafenib; *P<0.05, **P<0.01):

areas of AHF), n=6. Sections were taken from: control rats (PBS), DEN induced hepatic neoplasia in rats untreated (HCC group) or treated with sorafenib (HCC SB), safranal (HCC SF) individually or combined (HCC SF SB). The structure of tissues and cells need to be stained in order to be visible. Cellular components are normally stained with a different color for proper distinction and analysis. Hematoxylin stains nucleic acids (nucleus) with blue color. Eosin stains proteins (cytoplasm) with pink color. The stain reveals plentiful structural and functional information (Fischer et al., 2008). Normal structure and histology of liver as seen in the control group where the liver is organized into hexagonally shaped lobules with the central vein at lobular centers. Hepatocytes are arranged in single-cell thick plates that radiate out from the central vein. In the animal model that has been developed in this study, macroscopic nodules were observed in the livers of mainly DEN-induced groups (see FIG. 10). However, microscopic histological examination of livers of rats in DEN-induced group showed clear neoplastic changes such as altered hepatocellular foci (AHF). In the present study, AHF are usually distinguished as delineated areas of hepatocytes with altered staining properties.

FIG. 13 provides a quantitative analysis of the area of neoplastic foci for histology from DEN-induced hepatic neoplasia in rats that were untreated (HCC group) or treated with sorafenib (HCC+SB), safranal (HCC+SF) individually or combined (HCC+SF+SB). Statistical significance was

TABLE 3

| | Control PBS | HOC | HCC + sorafenib | HCC + safranal | HCC + safranal + sorafenib |
|---|---|---|---|---|---|
| ALT | 7.44 ± 0.67 | 14.10 ± 0.15$^{a**}$ | 13.42 ± 1.12 | 10.93 ± 0.2$^{b**,\, c*}$ | 9.22 ± 1.92$^{b**,c*}$ |
| AST | 9.00 ± 0.39 | 10.18 ± 1.69 | 11.14 ± 0.62 | 7.80 ± 2.02 | 10.98 ± 0.50 |

Anti-Tumorigenic and Anti-Proliferative Activities of Safranal on DEN Induced Rat Liver Tumors Liver Gross FIG. 10 includes representative images of livers on week 20 to demonstrate the antitumorigenic effect of safranal (n=6). Whole liver excised from control rats (PBS), DEN-induced hepatic neoplasia in rats untreated (HCC group) or treated with sorafenib (HCC SB), safranal (HCC SF) individually or combined (HCC SF SB). Control PBS liver shows normal liver structure and color with no macroscopic lesions. The treatments showed "lesser levels of damaged livers" compared to livers from HCC group. DEN caused lesions and rough liver surface and caused abnormality in liver color in HCC animals. Drug treatments of HCC rats restored to variable degrees the normal liver architecture where lesions were evidently less in drug-treated groups.

FIG. 11 provides a quantitative analysis of the number of liver nodules from DEN-induced hepatic neoplasia in rats untreated (HCC group) or treated with sorafenib (HCC+SB), safranal (HCC+SF) individually or combined (HCC+SF+ SB). Statistical significance was determined using Microsoft Excel Data Analysis Tool Pack, t-test: two-sample assuming equal variances (b versus HCC; *P<0.05, **P<0.01). Treatments with safranal (HCC+safranal) and with both safranal and sorafenib (HCC+safranal+sorafenib) reduced lesions comparing to HCC animals, safranal also dramatically decreased lesions comparing to treatment with sorafenib alone (HCC+sorafenib).

Histology

FIG. 12 includes representative images of hematoxylin and eosin-stained sections (arrows point to representative determined using Microsoft Excel Data Analysis Tool Pack, t-test: two-sample assuming equal variances (b versus HCC; P<0.01, *P<0.001). The analysis shows that safranal either alone or in combination with sorafenib seems to enhance (P<0.001) the restoration of the normal architecture of the liver in DEN-treated groups.

Reticulin Staining

FIG. 14 provides representative light microscope images of reticulin-stained sections (arrows point to reticulin fibers). The sections were taken from control rats (PBS), DEN-induced hepatic neoplasia in rats untreated (HCC group) or treated with sorafenib (HCC SB), safranal HCC SF) individually or combined (HCC SF SB). Control PBS liver shows normal liver morphology and defined reticular fibers. Liver sections from HCC animals show that DEN has caused reticular fiber breakage indicating hepatic neoplasia diagnosis. Treatment with safranal (HCC+safranal) and with both safranal and sorafenib (HCC+safranal+sorafenib) reduced reticular fibers' breakage and restored their morphology comparing to HCC group, with a higher improvement comparing to treatment with sorafenib alone (HCC+ sorafenib).

Anti-Proliferative Effect of Safranal

As shown in the western blot results of FIG. 15, safranal inhibits proliferation of induced hepatic neoplasia. FIG. 15A is a western blot analysis of the proliferation-related protein (PCNA) on DEN-induced hepatic neoplasia in rats untreated (HCC group) or treated with sorafenib (HCC SB), safranal (HCC SF) individually or combined (HCC SF+SB). In FIG. 15B, each band intensity was quantified using ImageJ, normalized in relative to the total protein from the liver.

Results are expressed as mean±S.D for n=4 animals in each group. Statistical significance was determined using Microsoft Excel Data Analysis Tool Pack, t-test: two-sample assuming equal variances. The results showed that PCNA was significantly (P<0.01) increased in DEN induced livers comparing to controls, while treatment with safranal (P<0.001) and with both safranal and sorafenib (P<0.05) significantly downregulated PCNA. Interestingly, the effect of safranal was more evident when applied alone compared to its combined administration with sorafenib, as well as compared to the effect of sorafenib alone.

Effect of Safranal on Cell Cycle Progression

To study the pathway responsible for safranal mediated cell cycle effect in DEN-induced rat liver neoplasia, the expression levels of cell cycle-related proteins were examined. Cdk1, cyclin B1, Cdc25B western blot results (FIG. 16) showed that they are significantly (P<0.01, P<0.01, P<0.05, respectively) increased in HCC animals as compared to control animals. Treatment in (HCC+safranal) and (HCC+safranal+sorafenib) groups significantly decreased their levels (P<0.001) comparing to HCC animals. Treatment with safranal (HCC+safranal) and the combination drug (HCC+safranal+sorafenib) showed a greater decrease than treatment with sorafenib alone (HCC+sorafenib) (FIG. 17). Without being bound to any particular theory, it is possible then that safranal may sensitize hepatic cells to sorafenib's effect by further decreasing the expression of cell cycle-related proteins in the co-treated group. These results suggest that safranal causes G2/M cell cycle arrest of drug-treated hepatic cells.

Effect of Safranal on Apoptosis

To study the pathway responsible for safranal mediated apoptosis in DEN-induced rat liver tumor cells, the expression levels of apoptosis-related proteins were examined in the western blot of FIG. 18. The results showed that safranal treatment significantly (P<0.05) increased the expression of the pro-apoptotic protein Bax and significantly (P<0.05) decreased the expression of the anti-apoptotic protein Bcl-2 compared to HCC groups. The Bax/Bcl-2 ratio favored the apoptotic effect of safranal (P<0.05) in DEN-induced rat liver tumors (FIG. 19). Interestingly, the apoptotic effect of safranal was more evident when administered alone compared to where both safranal and sorafenib, were administered or when sorafenib alone was used. To further investigate the apoptotic effect of safranal, western blot analysis showed that pro-caspase-9, pro-caspase-3, and PARP results confirmed caspase cascade activation and PARP cleavage, where the expression of pro-caspases-9 & 3 and whole PARP were significantly decreased compared to HCC group after treatments with safranal (P<0.01, P<0.001, P<0.001, respectively) and with both safranal+sorafenib (P<0.01, P<0.01, P<0.001, respectively) (FIG. 20). These results further support the pro-apoptotic effect of safranal on drug-induced neoplasia.

Effect of Safranal on TDP1 Expression

As set out in the in vitro studies reported above, topoisomerase I (TOP1) plays a key role in DNA replication and its inhibition may lead to DNA damage that can be protected by tyrosyl-DNA phosphodiesterase (TDP1) in complex with PARP. The western blot analysis of FIG. 21 shows that animal groups treated with safranal expressed lower levels of TDP1 whether alone or in combination with sorafenib.

Definitions

As used in this description and the accompanying claims, the following terms shall have the meanings indicated, unless the context otherwise requires:

As used herein, "treatment" is understood to refer to the administration of a drug or drugs to a patient suffering from cancer.

As used herein, the term "therapeutically effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

What is claimed is:

1. A method of treating, suppressing, or reducing the severity of hepatocellular carcinoma in a subject, the method comprising the steps of:

administering to the subject a composition comprising safranal or a pharmaceutically acceptable pro-drug thereof, wherein the pro-drug is selected from the group consisting of: a safranal salt, hemiacetal, acetal, thioacetal, silyether, tautomer, and combinations thereof, and a pharmaceutically acceptable carrier; and then administering to the subject topotecan in an amount ranging from 0.1:1 to 10:1 by weight, with respect to the content of the safranal of the composition;

wherein the safranal or its pro-drug is administered first to sensitize the hepatocellular carcinoma cells prior to exposure to the topotecan, and the topotecan is administered second, and wherein the safranal or its pro-drug is administered in a therapeutically effective amount sufficient to enhance cytotoxic effects of the topotecan on the hepatocellular carcinoma cells by reducing the IC50 of the topotecan by a sensitization factor of at least 73.

2. The method of claim 1, wherein the safranal is administered to the subject 24 to 48 hours prior to administration of the topotecan.

3. A therapeutic combination of drugs for the treatment of hepatocellular carcinoma, the combination comprising:

safranal or a pharmaceutically acceptable pro-drug thereof, wherein the pro-drug is selected from the group consisting of: a safranal salt, hemiacetal, acetal, thioacetal, silyether, tautomer, and combinations thereof;

a pharmaceutically acceptable carrier; and topotecan, wherein the amount of the topotecan is 0.1:1 to 10:1 by weight, with respect to the content of the safranal of the therapeutic combination, and wherein the safranal or its pro-drug and the topotecan are in separate pharmaceutical compositions and the safranal or its pro-drug is present in a therapeutically effective amount sufficient to reduce the IC50 of the topotecan against hepatocellular carcinoma cells by a sensitization factor of at least 73.

* * * * *